(12) United States Patent
McDowell, III

(10) Patent No.: US 12,178,446 B2
(45) Date of Patent: Dec. 31, 2024

(54) ADJUSTABLE TOURNIQUET TIE

(71) Applicant: KML Holding Group LLC, Quakertown, PA (US)

(72) Inventor: George R. McDowell, III, Hellertown, PA (US)

(*) Notice: Subject to any disclaimer, the term of this patent is extended or adjusted under 35 U.S.C. 154(b) by 0 days.

(21) Appl. No.: 18/346,764

(22) Filed: Jul. 3, 2023

(65) Prior Publication Data
US 2024/0000461 A1 Jan. 4, 2024

Related U.S. Application Data

(63) Continuation-in-part of application No. 17/667,720, filed on Feb. 9, 2022, which is a continuation-in-part of application No. 17/182,189, filed on Feb. 22, 2021, now Pat. No. 11,603,241, which is a continuation-in-part of application No. 16/202,508, filed on Nov. 28, 2018, now Pat. No. 10,926,929.

(60) Provisional application No. 62/593,908, filed on Dec. 2, 2017.

(51) Int. Cl.
*A61B 17/00* (2006.01)
*A61B 17/132* (2006.01)

(52) U.S. Cl.
CPC .................. *A61B 17/1327* (2013.01)

(58) Field of Classification Search
CPC .......... A61B 17/1327; B65D 2563/107; B65D 63/1072; H02G 3/32
See application file for complete search history.

(56) References Cited

U.S. PATENT DOCUMENTS

| | | | | |
|---|---|---|---|---|
| 1,771,689 | A * | 7/1930 | Owen | A61B 17/1327 606/203 |
| 3,855,669 | A * | 12/1974 | Meyer | B65D 63/1072 24/16 PB |
| 4,236,280 | A * | 12/1980 | Kreiseder | B65D 63/1072 24/301 |
| 6,185,791 | B1 * | 2/2001 | Khokhar | B65D 63/1063 24/16 PB |
| 7,017,237 | B2 * | 3/2006 | Magno, Jr. | F16L 3/2334 24/16 PB |
| 8,281,462 | B2 * | 10/2012 | Kuhne | B65D 63/1063 24/17 AP |
| 10,321,917 | B2 * | 6/2019 | Steinbaugh | A61B 17/1327 |
| D858,774 | S * | 9/2019 | Parsons | D24/169 |
| 2003/0229972 | A1* | 12/2003 | Welch | F16L 3/2332 24/16 PB |

(Continued)

*Primary Examiner* — David M Upchurch
(74) *Attorney, Agent, or Firm* — Douglas J. Ryder; Ryder, Mazzeo & Konieczny LLC

(57) ABSTRACT

A tie that can be adequately tighten so as to be used as a tourniquet that can be loosened when required. The tie includes an elongated strap having teeth formed thereon that engage with teeth in a locking head to allow movement in only one direction (tightening). A release tab in conjunction with a backplate enables the teeth in the locking head to be disengaged from the teeth on the elongated strap when the release tab is depressed so that the strap can move in an opposite direction (loosen the tourniquet). The release tab and the backplate are configured to face away from the body part to provide more room for engagement and provide necessary leverage to loosen the tie. A handle can be secured to the tie after it is secured around the body part to provide more leverage to adequately tighten the tie.

20 Claims, 20 Drawing Sheets

(56) References Cited

U.S. PATENT DOCUMENTS

| | | | |
|---|---|---|---|
| 2005/0049630 A1* | 3/2005 | Ambach | A61B 17/1327 606/203 |
| 2012/0053617 A1* | 3/2012 | Benz | A61B 17/1325 606/203 |
| 2015/0216536 A1* | 8/2015 | Hopman | A61B 17/1322 606/202 |
| 2018/0228497 A1* | 8/2018 | Dimino | A61F 15/006 |

* cited by examiner

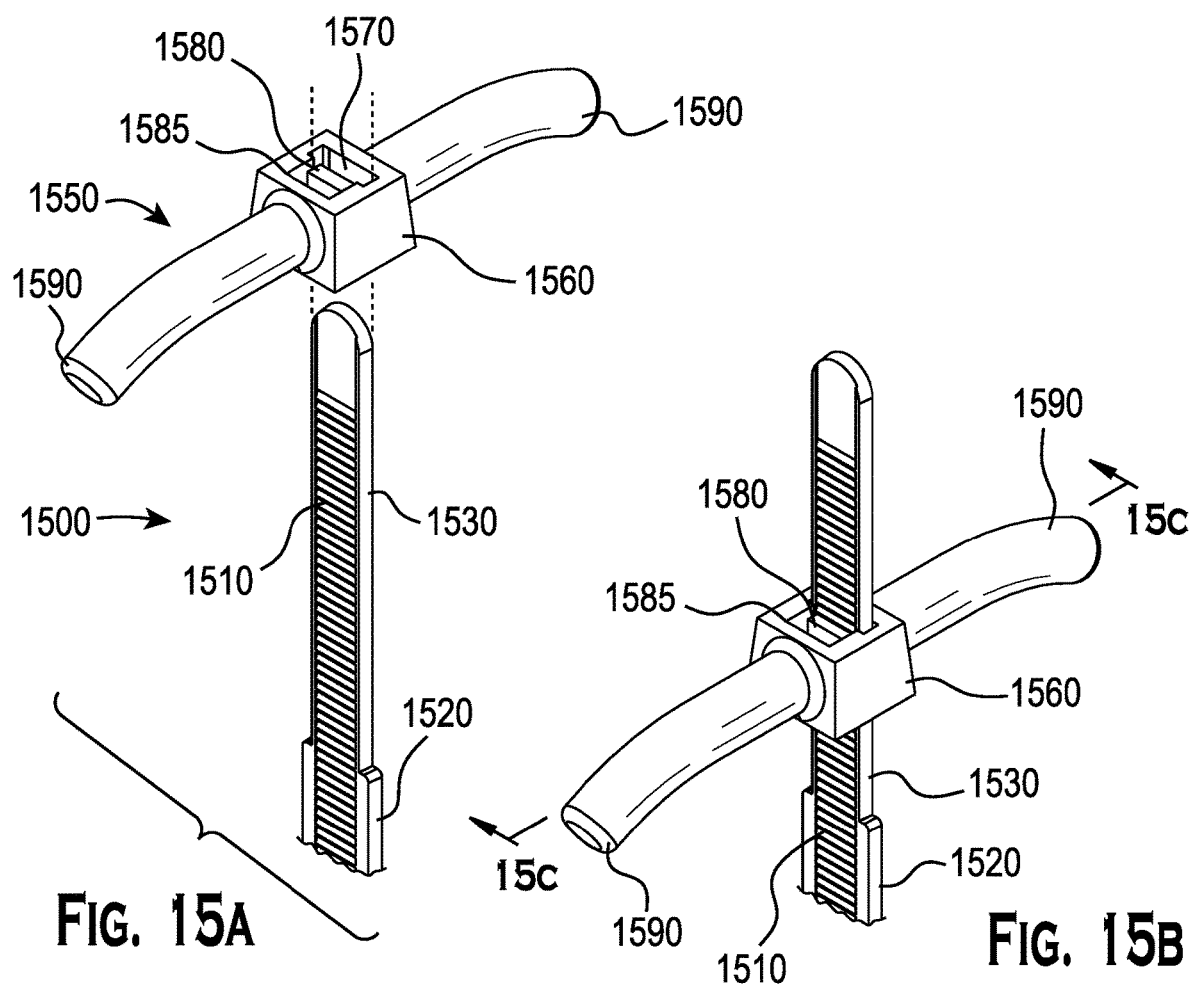
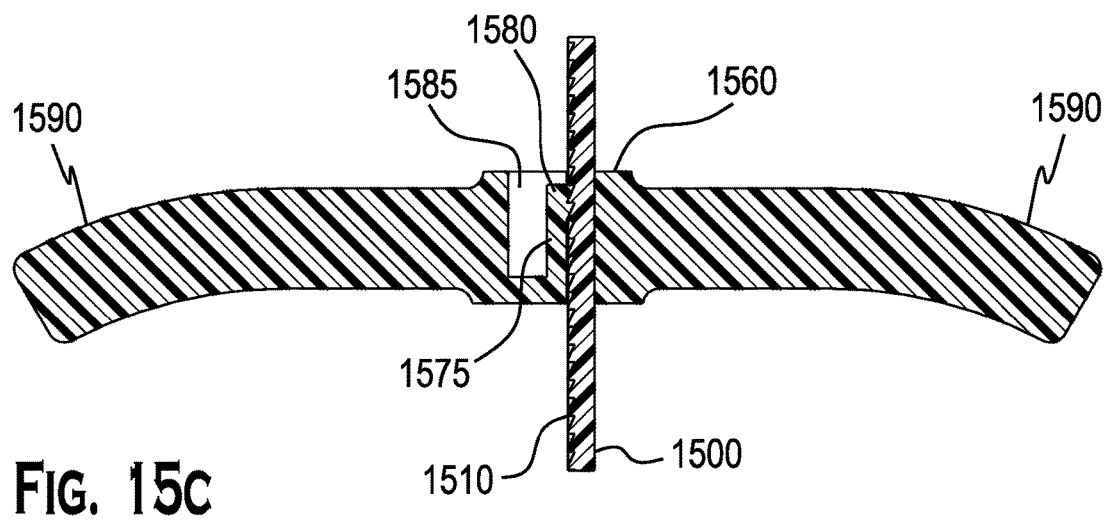

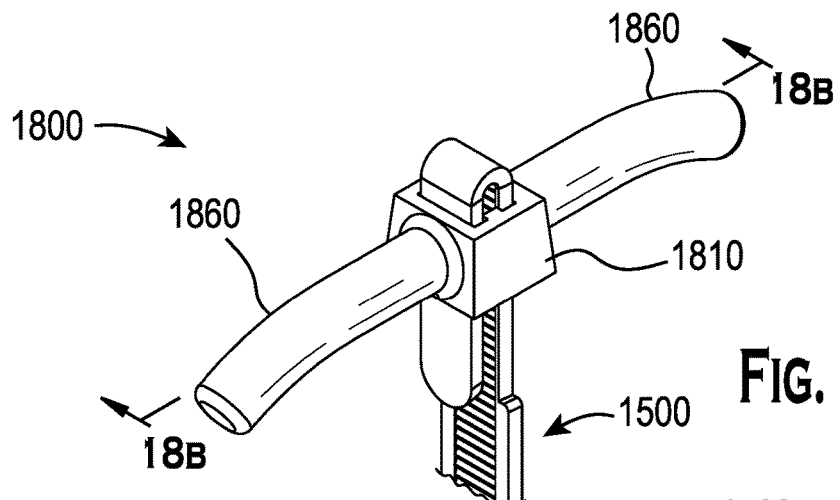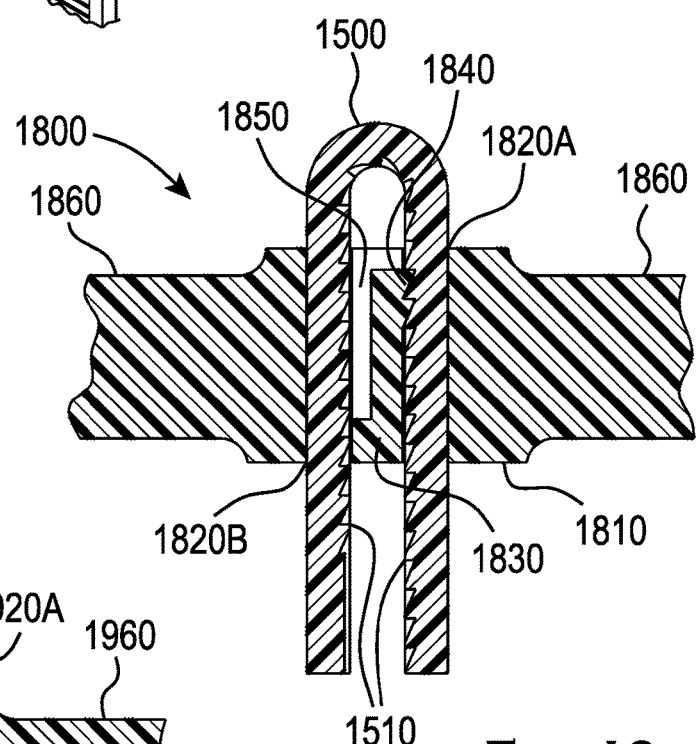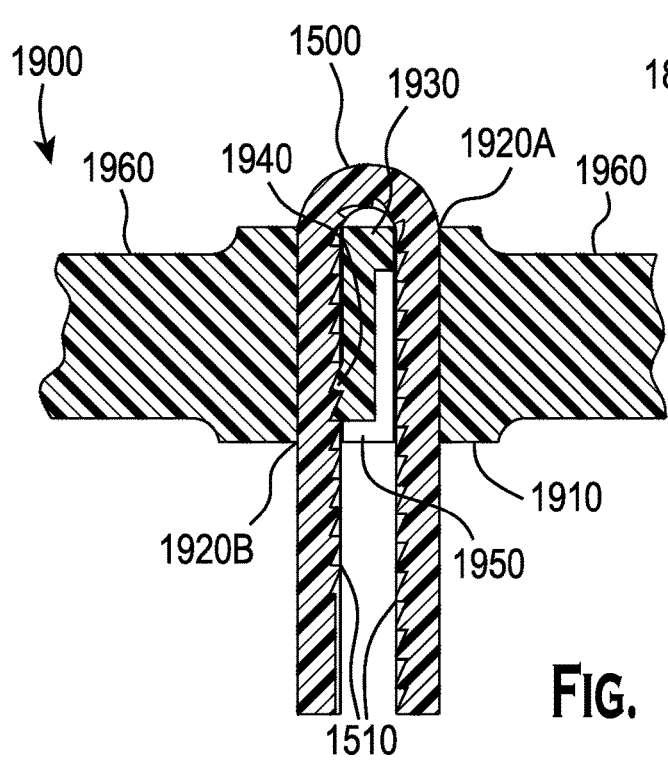

ADJUSTABLE TOURNIQUET TIE

PRIORITY

This application is a continuation-in-part (CIP) of and claims the benefit under 35 U.S.C. § 120 of U.S. patent application Ser. No. 17/667,720 filed Feb. 22, 2022 (U.S. Pat. No. 11,691,796 issued on Jul. 4, 2023). Application Ser. No. 17/667,720 is a CIP of and claims the benefit under 35 U.S.C. § 120 of U.S. patent application Ser. No. 17/182,189 filed Feb. 22, 2021 (U.S. Pat. No. 11,603,241 issued on Mar. 14, 2023). Application Ser. No. 17/182,189 is a CIP of and claims the benefit under 35 U.S.C. § 120 of U.S. patent application Ser. No. 16/202,508 filed Nov. 28, 2018 (U.S. Pat. No. 10,926,929 issued on Feb. 23, 2021). U.S. application Ser. No. 16/202,508 claims the priority under 35 U.S.C. § 119 of U.S. Provisional Patent Application 62/593,908 filed on Dec. 2, 2017. Application Ser. Nos. 17/667,720; 17/182,189; 16/202,508 and 62/593,908 are incorporated herein by reference in their entirety.

BACKGROUND

Zip ties are used to tie, fasten and/or connect various items. A typical zip tie includes an elongated body with teeth and a head through which the body may traverse in a single direction associated with tightening the tie. The zip tie is placed around the item(s) and is then tightened by placing the body through the head until the desired tightness is achieved. The typical zip tie cannot be loosened and can only be removed by cutting the tie. Cutting the zip tie may damage the item(s) that are secured thereby. Accordingly, zip ties may not be used with certain items.

Certain types of cuts and wounds (e.g., larger ones, ones located on arteries) may result in the loss of blood to an individual. Such cuts/wounds may require packing with gauze and using a tourniquet to secure the gauze in place and/or restrict blood flow to the area. Tourniquets provide the ability to tightly wrap around an area and be capable of being loosened or removed at an appropriate time. Various types of tourniquets are available for use. Some tourniquets include a means for tightening and securing the tourniquet after it is placed around the affected area. The means for tightening and securing may vary. Other tourniquets may be made of flexible material that can be stretched in order to be placed on the area and then once released may tighten on the area.

If an actual tourniquet is not available, different items may be used for the same purpose. For example, a belt could be used to wrap around the area and be pulled tight and locked in place with the buckle. Other materials (e.g., shirts, sheets) could be used to wrap around the area and then tied tight. A stick or the like could be connected to one end of the material and twisted in order to tighten the material.

Appropriately sized zip ties could be used as a tourniquet as they could be wrapped around and area and then pulled tight and secured in place. However, typical zip ties are not used as tourniquets because they cannot be loosened. As such, if the zip tie was tightened too much or if the zip tie had been on the area for more than a defined amount of time, it would not be easy to loosen the tie to prevent irreparable damage to the area. Releasable ties have been proposed but they are not designed to be easily released as may be desired for a tourniquet. Typical releasable ties do not provide a configuration that provides an arrangement where the release mechanism faces away from the item (e.g., body part) secured to provide easy access for loosening the tie.

Typical ties may be pulled tight when a user has access to a side of the strap on each end of the locking head. However, if only the end pulled through the locking head was available for pulling (as may be the case if used as a tourniquet) a typical tie may not provide sufficient leverage to get the tie tight enough.

BRIEF DESCRIPTION OF THE DRAWINGS

The structure, objects, and advantages of the releasable tie will be understood by referring to the detailed description of illustrative embodiments in conjunction with the accompanying technical drawings, in which:

FIGS. 15A-D illustrate several views of an example releasable tie and an example tightening handle, according to one embodiment.

FIGS. 18A-B illustrate perspective and cross-sectional views of an example releasable tie and an example tightening handle, according to one embodiment.

FIG. 19 illustrates a cross sectional view of an example releasable tie and an example tightening handle, according to one embodiment.

DETAILED DESCRIPTION

A zip tie capable of being used as a tourniquet. The zip tie is configured to be pulled tight around a patient's body part (e.g., limb) by a user (e.g., first responder) and loosened as required. The zip tie includes an elongated strap having teeth formed thereon that engage with teeth in a locking head to allow movement in only one direction (tightening). The locking head also includes a releasing mechanism that enables the teeth in the locking head to be disengaged from the teeth on the elongated strap so that the strap can move in an opposite direction that enables loosening of the strap. The release mechanism is configured to face away from the body part the strap is wrapped around to provide more room for engagement (e.g., by a user's hand), enable a user to engage therewith while wearing gloves, provide necessary leverage to release the zip tie without need to press the tie against the body part, and provide an option for securing excess strap therewithin.

Figure 1A:
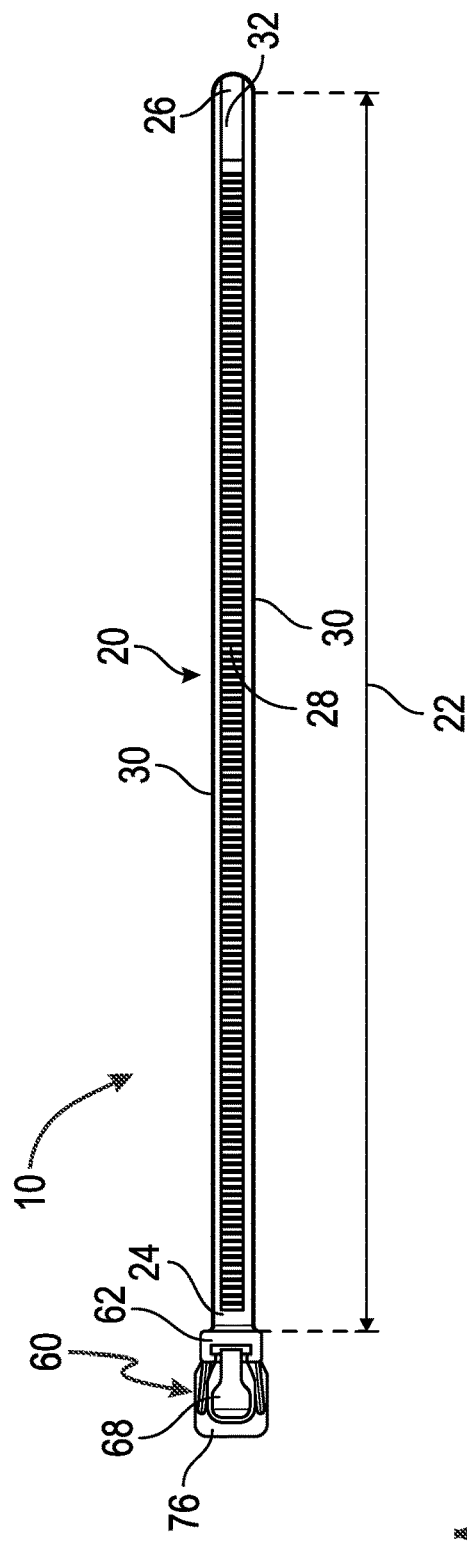
FIGS. 1A-B illustrate top views of an example releasable tie in open configurations, according to one embodiment.
Figure 1B:
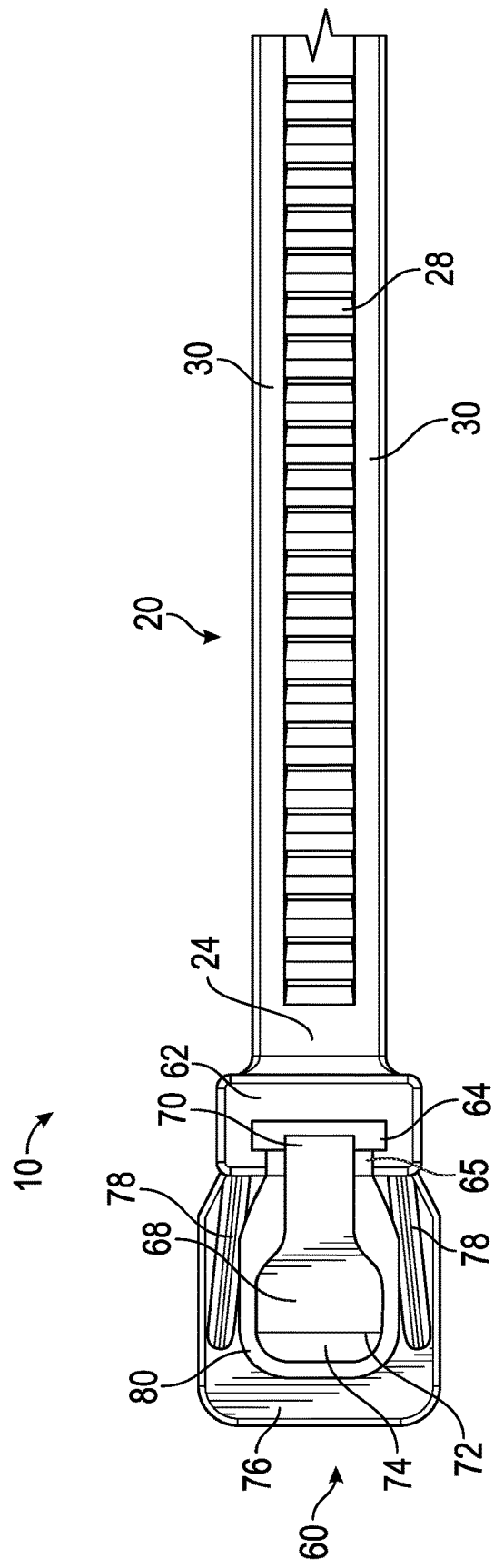

FIG. 1A illustrates top view and FIG. 1B illustrates a close-up top view of an example releasable tie 10 that can be used as a tourniquet. The tie 10 includes an elongated planar strap 20 and a releasable locking head 60. The strap 20 has an elongated length 22 that traverses from a first end 24 to a second end 26. A first side (e.g., top side) of the strap 20 includes teeth 28 formed within guide rails 30. The strap teeth 28 may be saw tooth shaped where one side is flat and the other side is angled. The first end 24 is connected to the locking head 60. The second end 26 of the of strap 20 includes a tongue 32 (with no teeth) that assists in guiding the strap 20 into the locking head 60.

The locking head 60 includes a main body 62 (wider than the strap 20) having a passthrough 64 formed therein from a first side to a second side (e.g., top to bottom). The passthrough 64 is sized to enable the strap 20 to pass therethrough. When the strap 20 passes through the passthrough 64 the locking teeth 28 will point toward a far end of the passthrough 64 (end away from the strap 20). A first side (top) of the main body 62 includes an opening 65 between the passthrough 64 and the far end of the main body. Extending through the opening 65 and into the passthrough 64 and pointing toward a near end (end close to strap 20) are one or more locking head teeth 66 to engage with the strap teeth 28. It should be noted, the one or more locking head teeth 66 and the strap teeth 28 within the pass through 64 are not visible in the top views of FIGS. 1A-B. The engagement of the one or more locking head teeth 66 and the strap teeth 28 within the pass through 64 enable the strap 20 to pass through the passthrough 64 in a first direction (tightening) but not in a second direction (loosening).

A release tab 68 extends from a far end of the first side (top) of the main body 62 in a direction away from the strap 20 (e.g., substantially parallel to strap 20 in a steady state). The opening 65 enables a first end 70 of the release tab 68 to extend into the passthrough 64 and connect to the one or more locking head teeth 66. A second end 72 of the release tab 68 is wider than the first end 70 to provide a larger surface for receiving at least a portion a finger (e.g., thumb) of a user. The second end 72 of the release tab 68 may include a ripple strip (raised portion) 74 to provide the user an indication their finger is at the end thereof and potentially prevent the user's finger from slipping off and/or to assist in maintaining the users finger thereon. While not visible in FIGS. 1A-B, when the release tab 68 is engaged (pressed downward), the first end 70 pivots upward and outward from the passthrough 64 and the one or more one or more locking head teeth 66 pivot toward a far end of the passthrough 64 so as to disengage from the strap teeth 28 and enable the strap 20 to move through the passthrough 64 in the second direction (be loosened).

A backplate 76 extends from a second side (bottom) of the main body 62 in a direction away from the strap 20 (e.g., substantially parallel to the strap 20 and also substantially parallel to the release tab 68 when not being depressed). The backplate 76 may be connected to, and extend from, the sides of the bottom of the main body 62. According to one embodiment, the backplate 76 may get wider as it extends from the main body 62. The backplate 76 may be wider and longer than the release tab 68 and have substantially the same shape. To provide support for the backplate 76, sidewalls 78 may extend from sides of the main body 62 and connect to the backplate 76. The sidewalls 78 may be angled downward from the main body 62 as will be more visible in side views.

The backplate 76 is configured to receive at least a portion of a user's finger (e.g., index finger) to enable a user to provide support (e.g., resistance) when the release tab 68 is being depressed. According to one embodiment, the backplate 76 may include an opening 80 formed therein. The opening 80 may be larger than the release tab 68 and have substantially the same shape as the release tab 68. The opening 80 ensures that the backplate 76 does not interfere with the depressing of the release tab 68. The opening 80 may also provide an edge for a user's finger to secure thereto to potentially prevent the user's finger from slipping off and/or to assist in maintaining the users finger thereon.

Figure 2A:
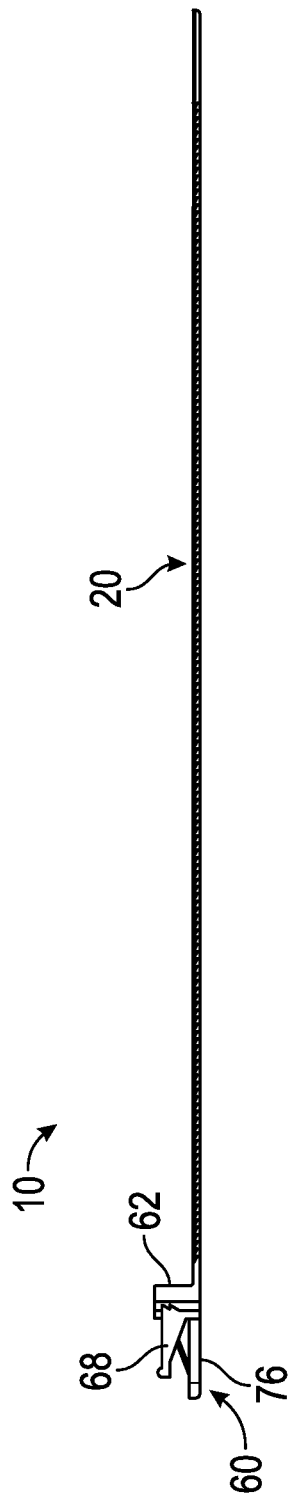
FIGS. 2A-B illustrate cross sectional side views of an example releasable tie in open configurations, according to one embodiment.
Figure 2B:
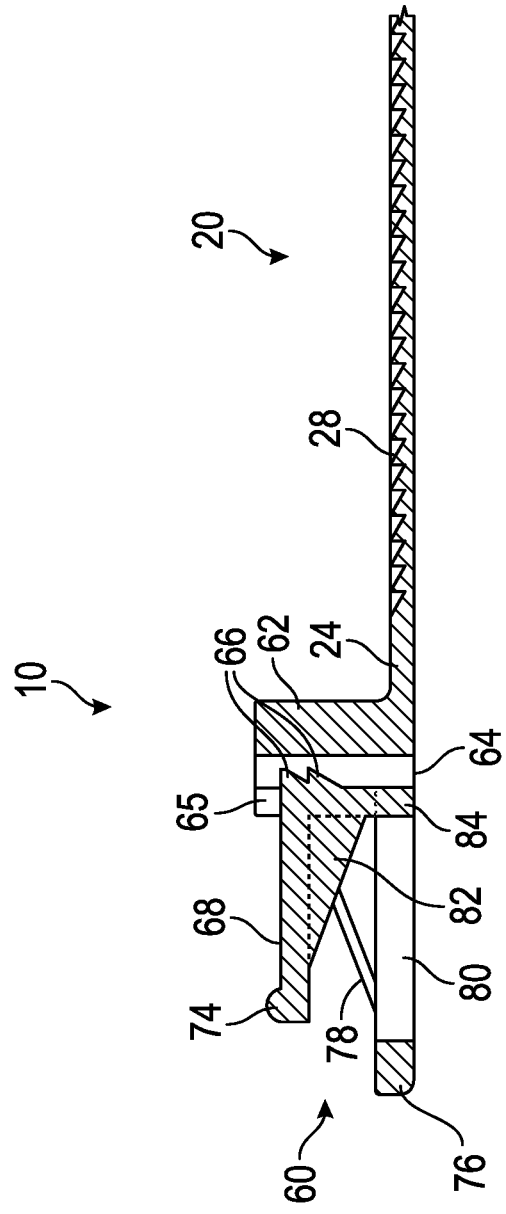

FIG. 2A illustrates a cross-sectional side view and FIG. 2B illustrates a close-up cross-sectional side view of the example releasable tie 10. The one or more locking head teeth 66 (two illustrated but not limited thereto) extend into the passthrough 64 and point toward a near side thereof. The one or more locking head teeth 66 are connected to a first end 70 of the release tab 68 which enters the passthrough 64 via the opening 65 and traverses away from the main body 62 and the strap 20. The release tab 68 includes the ripple strip 74 at the second end 72 thereof. The release tab 68 may include a support 82 centrally located that diagonally extends from a point in proximity to the second end 72 to a fulcrum 84 that is located under the one or more locking head teeth 66. The fulcrum 84 acts as a pivot point so that when the release tab 68 is depressed, the one or more locking head teeth 66 move upward and backward until they disengage with the one or more strap teeth 28. When the teeth 66 and the teeth 28 are disengaged the strap 20 may be loosened.

The backplate 78 extends from the main body 62 past the release tab 68. The opening 80 in the backplate 78 extends from the main body 62 (or a point close thereto) until past the release tab 68 so as to not interfere with the release tab 68 being depressed and to provide the other potential benefits discussed above.

Figure 3:
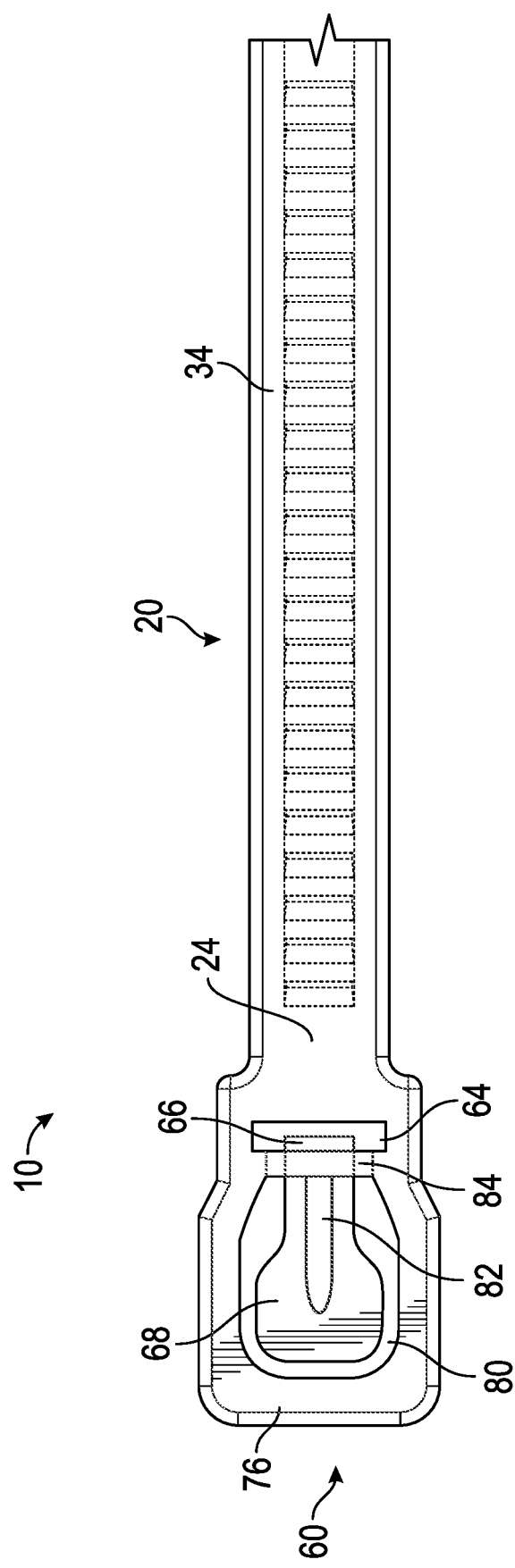
FIG. 3 illustrates a bottom view of an example releasable tie in an open configuration, according to one embodiment.

FIG. 3 illustrates a bottom view of the example releasable tie 10. The opening 80 in the backplate 78 is clearly shown larger than the release tab 68. The opening 80 may enable excess strap 20 to be secured therein (see for example FIGS. 6A-B). The last of the one or more locking head teeth 66 can be seen extending into the opening 64. The fulcrum 84 can be seen in front of the passthrough 64 below the one or more locking teeth and the first end of the release tab 68. The support 82 is shown extending to the fulcrum 84. An underside 34 of the strap 10 may be smooth opposite the teeth 28 on the topside.

Figure 4:
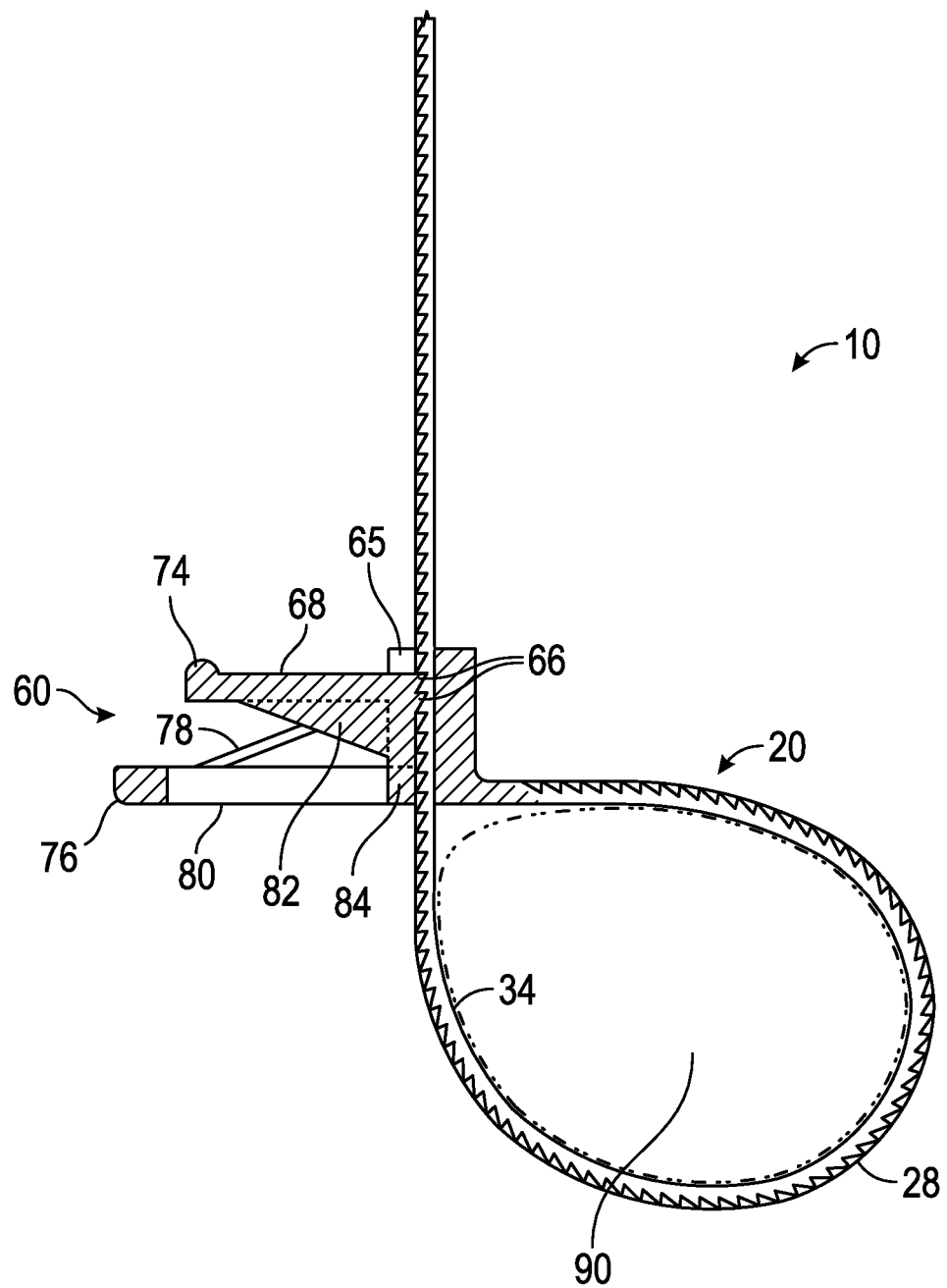
FIG. 4 illustrates a cross sectional side view of an example releasable tie in a closed (tied) configuration, according to one embodiment.

FIG. 4 illustrates cross-sectional side view of the example releasable tie 10 in a locked position. When the strap 20 passes through the locking head 60 a loop 90 is formed for tightening around a patient's body part (no body part illustrated) to act as a tourniquet. The strap teeth 28 are located on an outside of the loop 90 and the bottom 34 of the strap faces the loop 90 and the body part secured therein. As illustrated, the bottom 34 is smooth so that there is no impact to the body part when tightened. The release tab 68 and the backplate 76 of the locking head 30 extend substantially perpendicular to the strap 20 in a direction away from the loop 90. The location of the release tab 68 and the backplate 76 provides a user easy access thereto.

Figure 5:
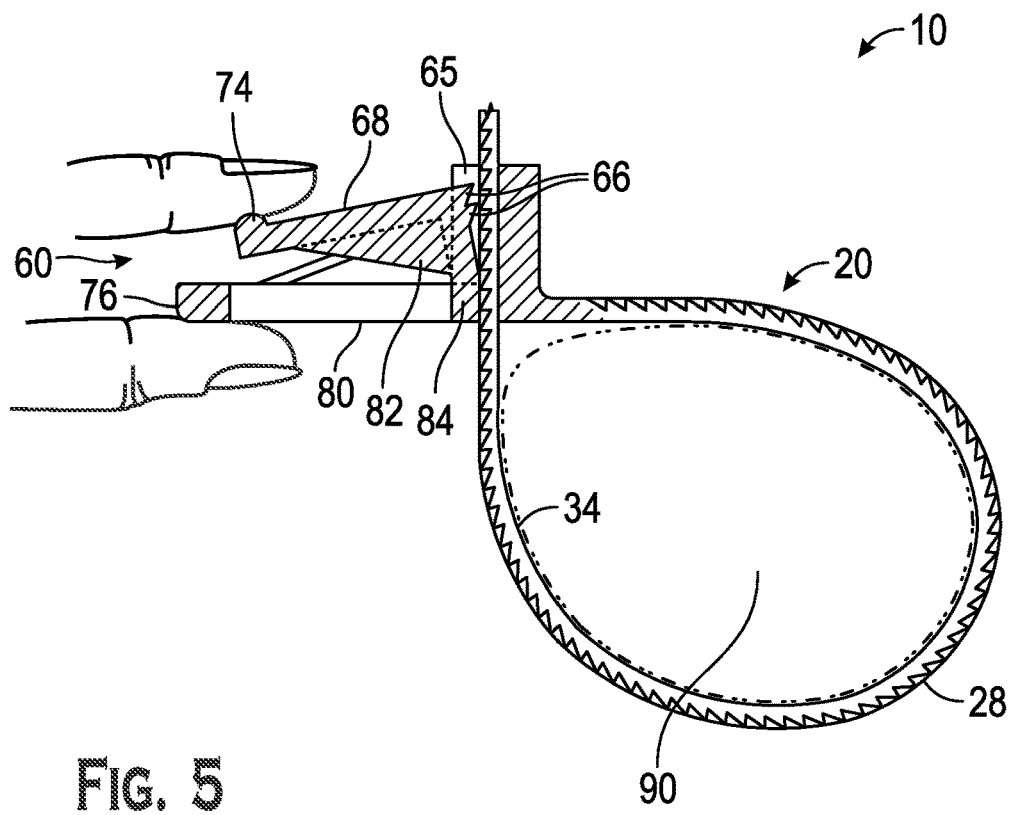
FIG. 5 illustrates a cross sectional side view of an example releasable tie in a closed (tied) configuration being released utilizing two fingers, according to one embodiment.

FIG. 5 illustrates a cross sectional side view of the strap 10 in a closed configuration where a first finger is utilized to push the release tab 68 downward and a second finger is located below the backplate 76 to provide support (leverage) thereto. Once the release tab 68 is depressed and the teeth 66 are disengaged from the teeth 28, the strap 20 can be moved in a release direction to expand the loop 90 in order to remove pressure on the body part. As the locking head 60 is held by the two fingers, the locking head 60 may actually be moved with respect to the strap 20. As illustrated, the locking head 60 may be moved in an upward direction to expand the loop 90. The use of the release tab 68 and the backplate 76 extending away from the loop 90 for easy access and the relatively large size thereof to receive fingers enables the releasable tie 10 to be easily loosened as needed. Furthermore, the releasable tie 10 may be operated in tight spaces and whether the user is wearing gloves or not.

The example releasable tie 10 preferably is molded in one piece integrally from thermoplastic, such as nylon or polypropylene and possesses sufficient strength and resiliency to enable it to be used as a tourniquet.

Figure 6A:
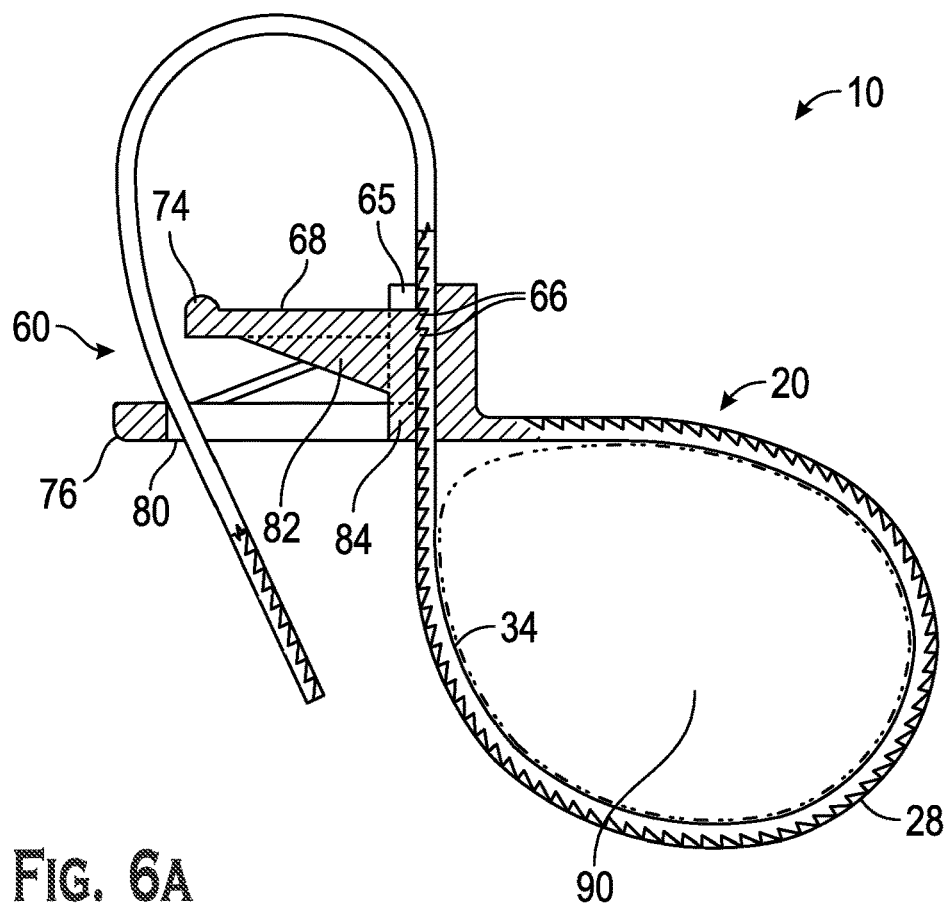
FIGS. 6A-B illustrate cross sectional side views of an example releasable tie in closed configurations where excess strap is tucked within an opening in a backplate of the locking head, according to various embodiments.
Figure 6B:
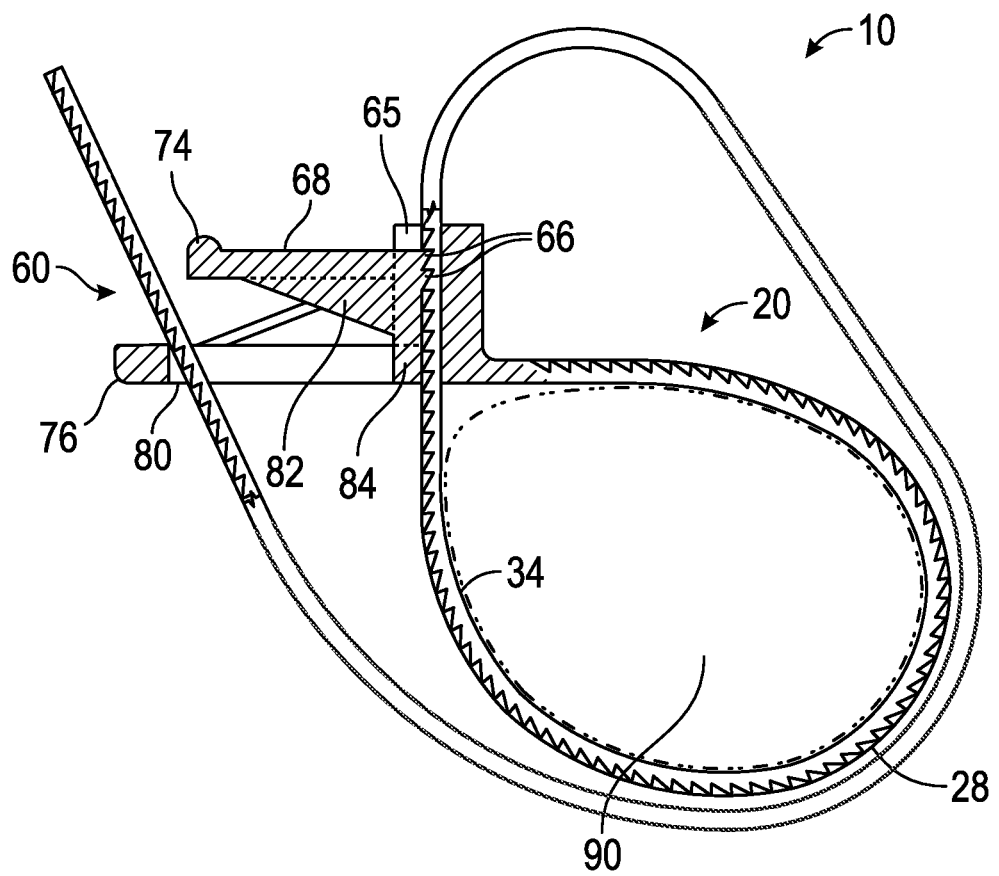

According to one embodiment, the opening 80 may enable excess strap 20 (portion of strap 20 that passed through the locking head 60) to be secured therein. The tucking of the excess strap 20 may prevent the excess strap 20 from getting in the way and/or getting caught on something. As illustrated in FIG. 6A, the excess strap 20 is looped back and tucked in the top of the opening 80. This arrangement covers the release tab 68 and may provide a barrier to the release tab 68 inadvertently being depressed and loosening the strap 20. As illustrated in FIG. 6B, the excess strap 20 is wrapped around the body part being secured therein and is tucked into the bottom of the opening 80.

Figures 7, 8:
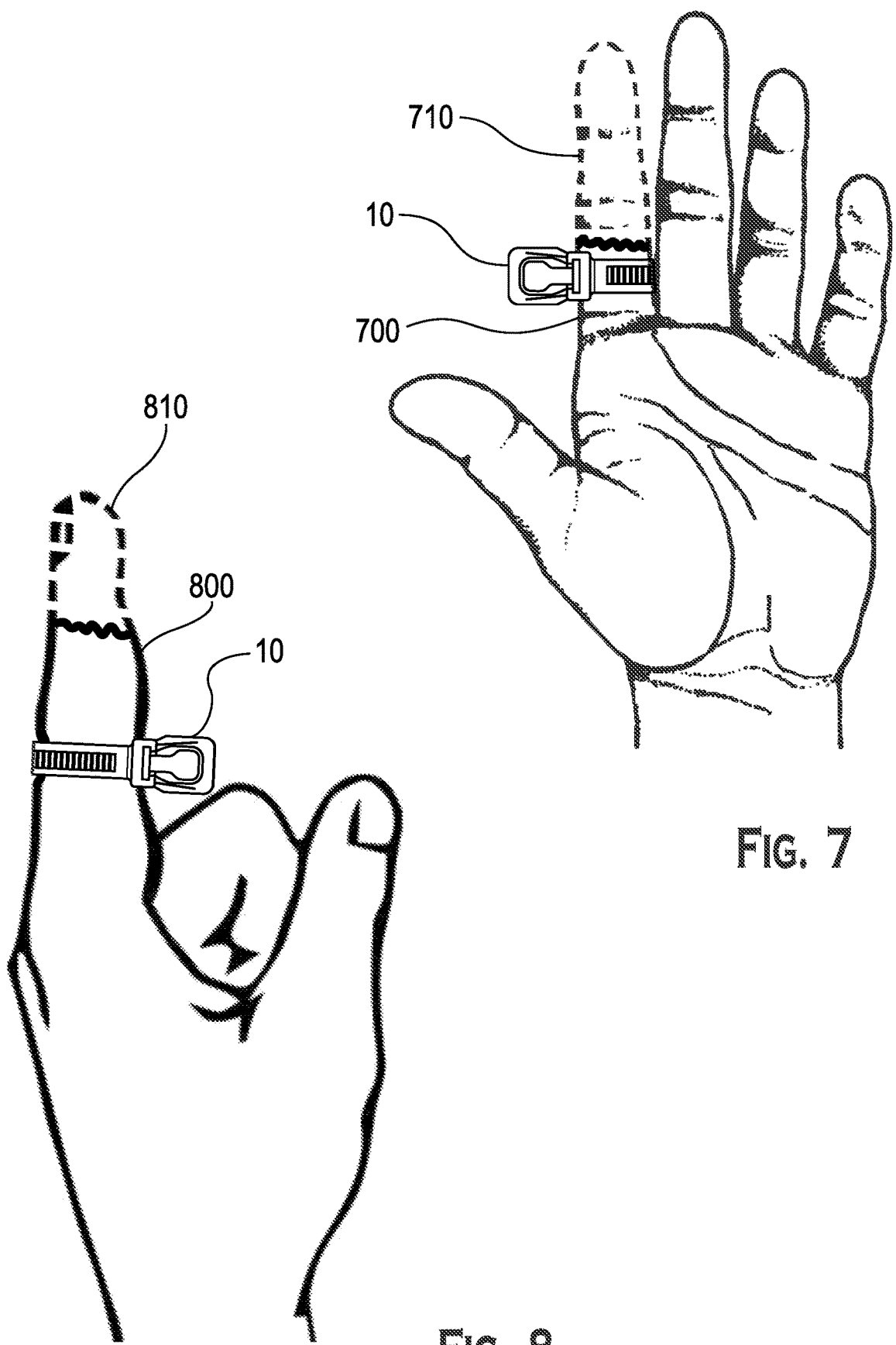
FIG. 7 illustrates a front view of an example releasable tie used as a tourniquet for an amputated finger, according to one embodiment.
FIG. 8 illustrates a side view of an example releasable tie used as a tourniquet for an amputated finger, according to one embodiment.

FIG. 7 illustrates a front view of an example releasable tie 10 being used as a tourniquet on an amputated finger 700. The finger 700 has been amputated around the middle knuckle so that the distal and middle phalanges are the portion that was amputated. The amputated portion 710 is illustrated with a dotted line. The tie 10 is secured to the finger 700 below the amputation. The tie 10 would be tightened a sufficient amount to stop, or at least restrict, the blood flow therefrom.

FIG. 8 illustrates a side view of an example releasable tie 10 being used as a tourniquet on an amputated finger 800. The finger 800 has been amputated around the upper knuckle so that the amputated portion 810 (illustrated with a dotted line) is the distal phalange. The tie 10 is secured to the finger 800 below the amputation. The tie 10 would be tightened a sufficient amount to stop, or at least restrict, the blood flow therefrom.

Figure 9:
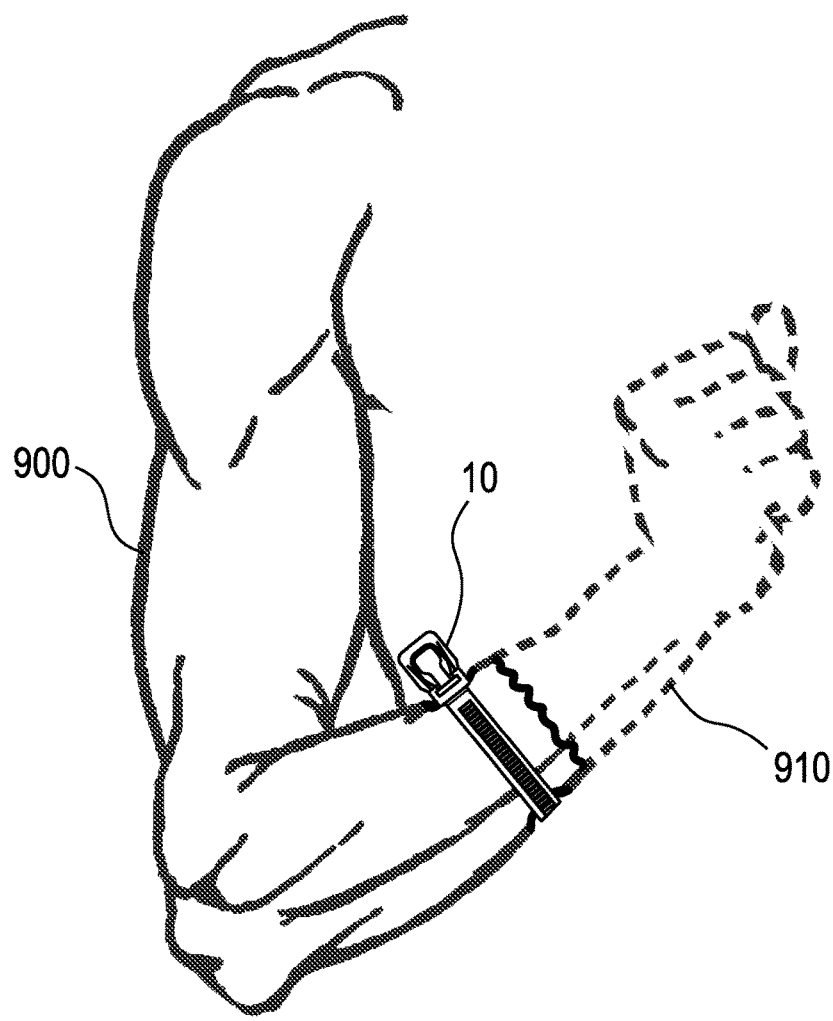
FIG. 9 illustrates a front view of an example releasable tie used as a tourniquet for an amputated arm, according to one embodiment.

FIG. 9 illustrates a front view of an example releasable tie 10 being used as a tourniquet on an amputated arm 900. The arm 900 has been amputated around the middle of the forearm so that the hand and a portion of the forearm are the portion of the arm that was amputated. The amputated portion 910 is illustrated with a dotted line. The tie 10 is secured to the arm 900 below the amputation. The tie 10 would be tightened a sufficient amount to stop, or at least restrict, the blood flow therefrom.

Figure 10:
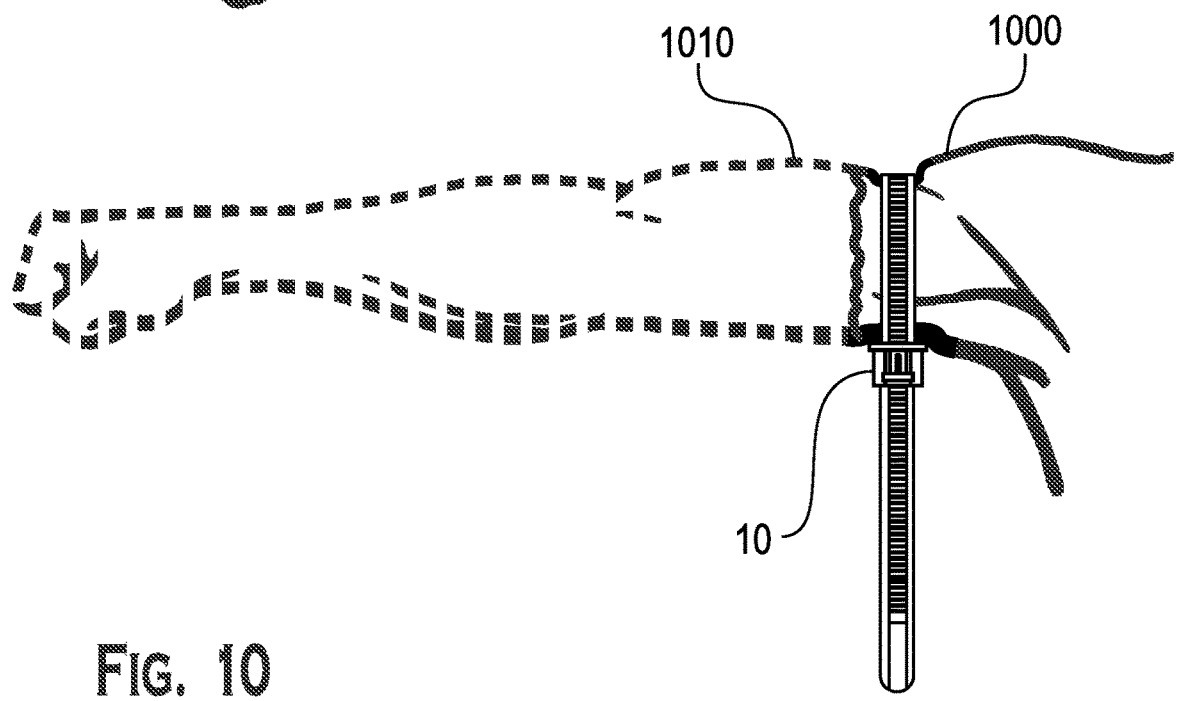
FIG. 10 illustrates a side view of an example releasable tie used as a tourniquet for an amputated arm, according to one embodiment.

FIG. 10 illustrates a side view of an example releasable tie 10 being used as a tourniquet on an amputated arm 1000. The arm 1000 has been amputated around the shoulder so that the amputated portion 910 (illustrated with a dotted line) is the bicep, forearm and hand. The tie 10 is secured to the arm 800 below the amputation. The tie 10 would be tightened a sufficient amount to stop, or at least restrict, the blood flow therefrom.

Figure 11:
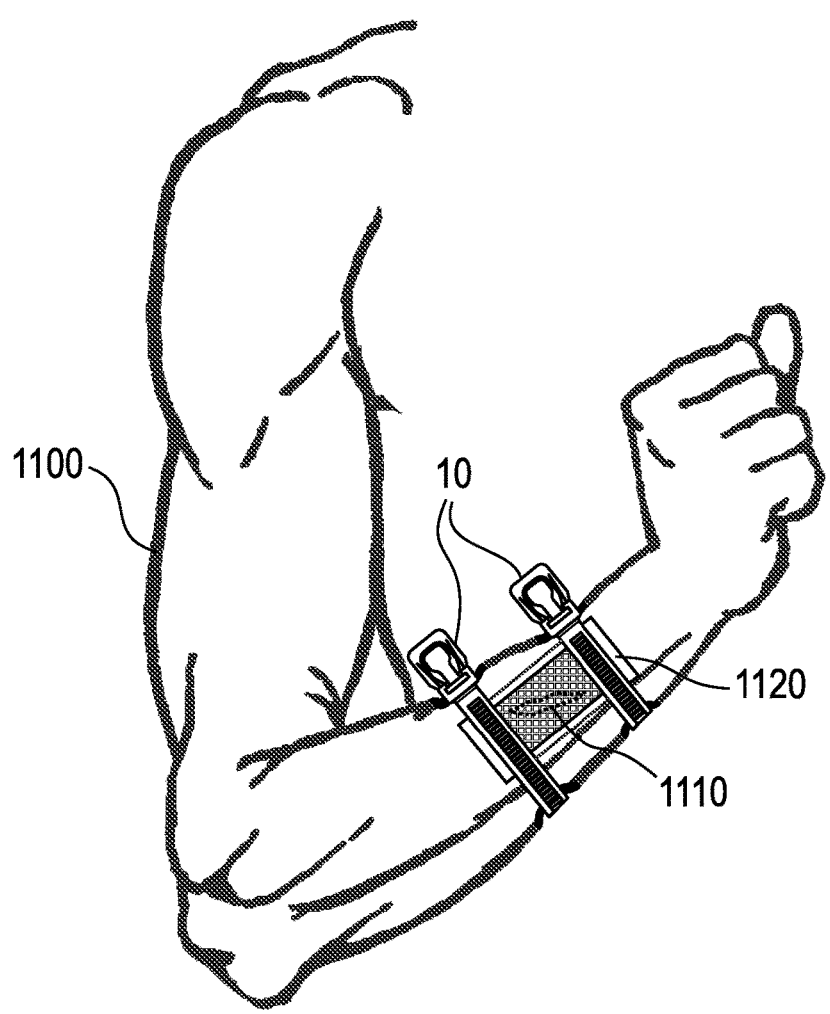
FIG. 11 illustrates a front view of example releasable ties used to secure gauze to a laceration on an arm, according to one embodiment.

FIG. 11 illustrates a front view of example releasable ties 10 being used to secure gauze 1120 to a laceration 1110 on an arm 1100. The laceration 1110 is located around the middle of the forearm. The gauze 1120 is placed over the laceration 1110 and is then secured to the arm 1100 using one or more ties 10. Two ties 10 are illustrated with one on each side of the laceration 1110. The number and location of the ties 10 is in no way intended to be limited thereby. Rather, any number and arrangement of ties required to secure the gauze 1120 could be used without departing the current scope.

Figure 12:
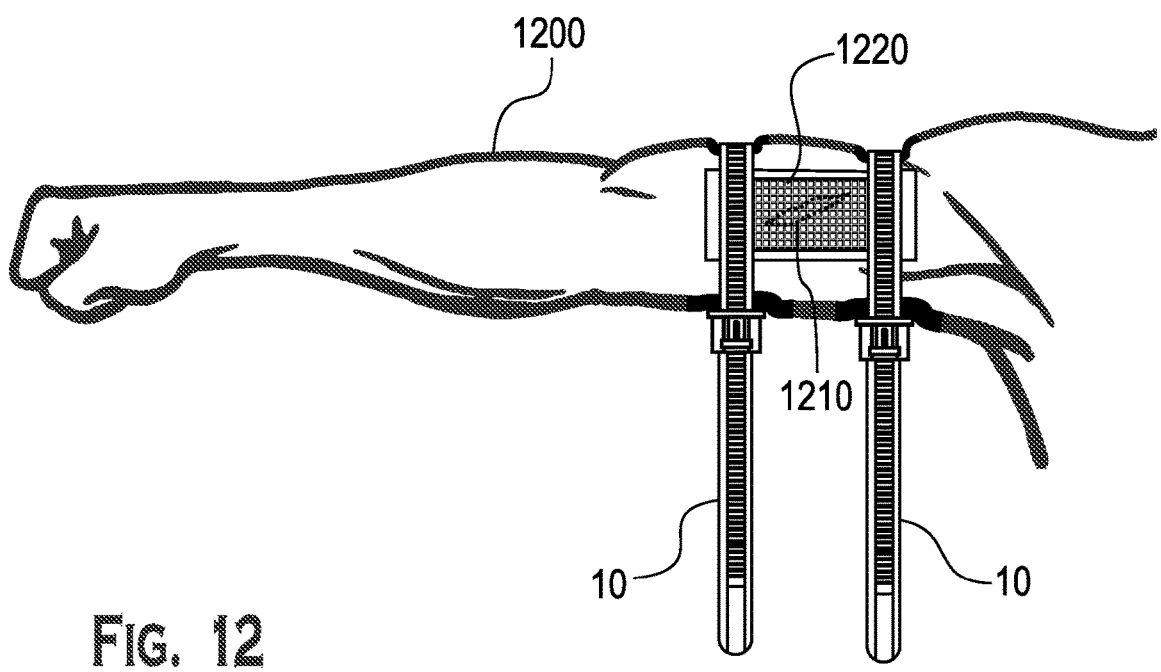
FIG. 12 illustrates a side view of example releasable ties used to secure gauze to a laceration on an arm, according to one embodiment.

FIG. 12 illustrates a side view of example releasable ties 10 being used to secure gauze 1220 to a laceration 1210 on an arm 1200. The laceration 1210 is located around the bicep. The gauze 1220 is placed over the laceration 1210 and is then secured to the arm 1200 using one or more ties 10. Two ties 10 are illustrated with one on each side of the laceration 1210 (not limited to this arrangement).

Figure 13:
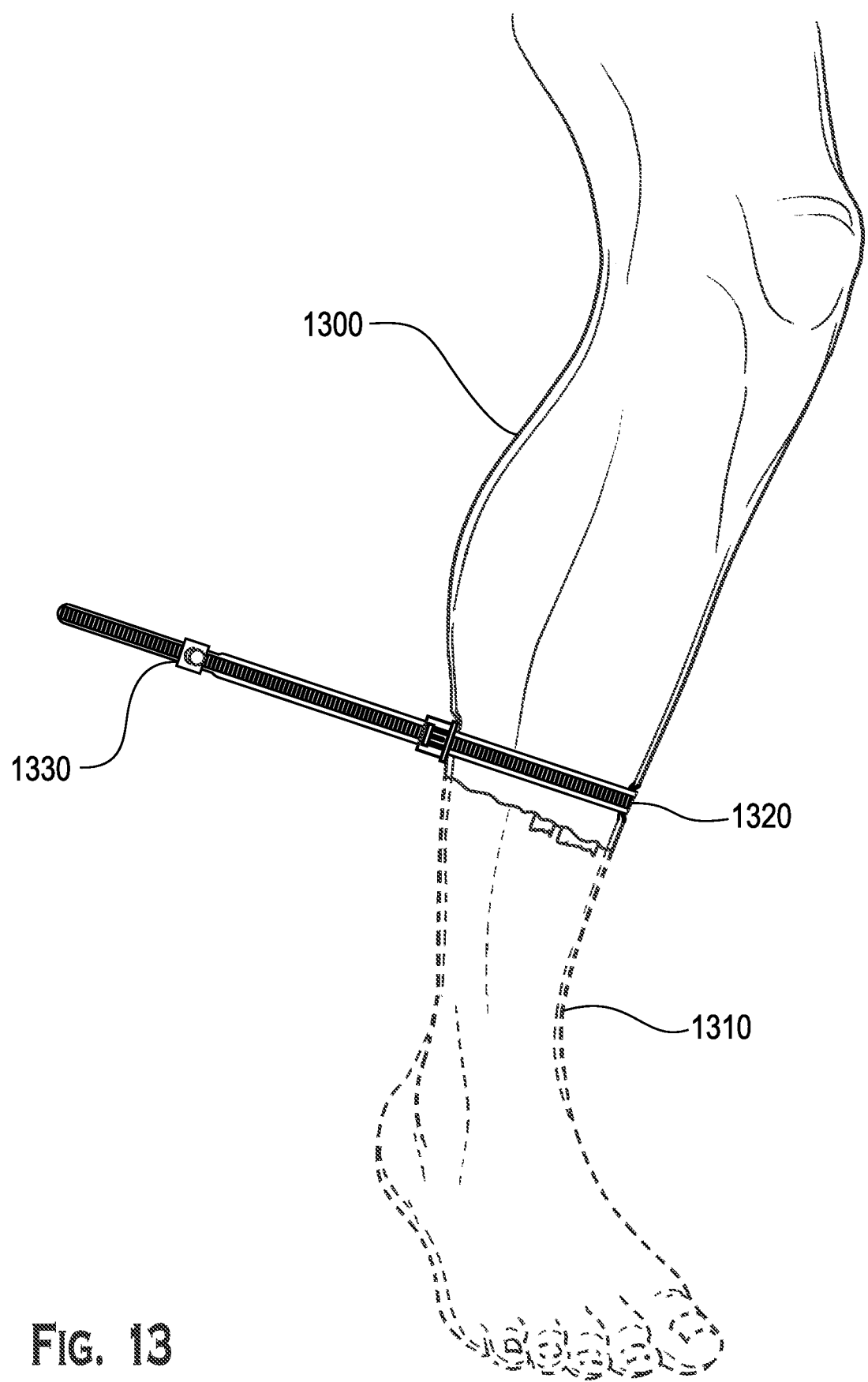
FIG. 13 illustrates a front view of an example releasable tie used as a tourniquet for an amputated leg, according to one embodiment.

FIG. 13 illustrates a front view of an example releasable tie 1320 being used as a tourniquet on an amputated leg 1300. The leg 1300 has been amputated around the middle of the lower leg (calf) so that the foot and a portion of the lower leg are the portion of the leg that was amputated. The amputated portion 1310 is illustrated with a dotted line. The tie 1320 is secured to the leg 1300 below the amputation. In order to ensure that the tie 1320 can be tightened a sufficient amount to stop, or at least restrict, the blood flow therefrom, the tie 1320 may be designed to have a handle 1330 secured to the strap (not separately labeled) after the tie 1320 has been wrapped around the leg 1300. A side view of the handle 1330 is illustrated in FIG. 13. A user may secure the handle 1330 to the strap and then use the handle 1330 to provide a sufficient amount of leverage and grip to pull the tie 1320 tight enough.

Figure 14:
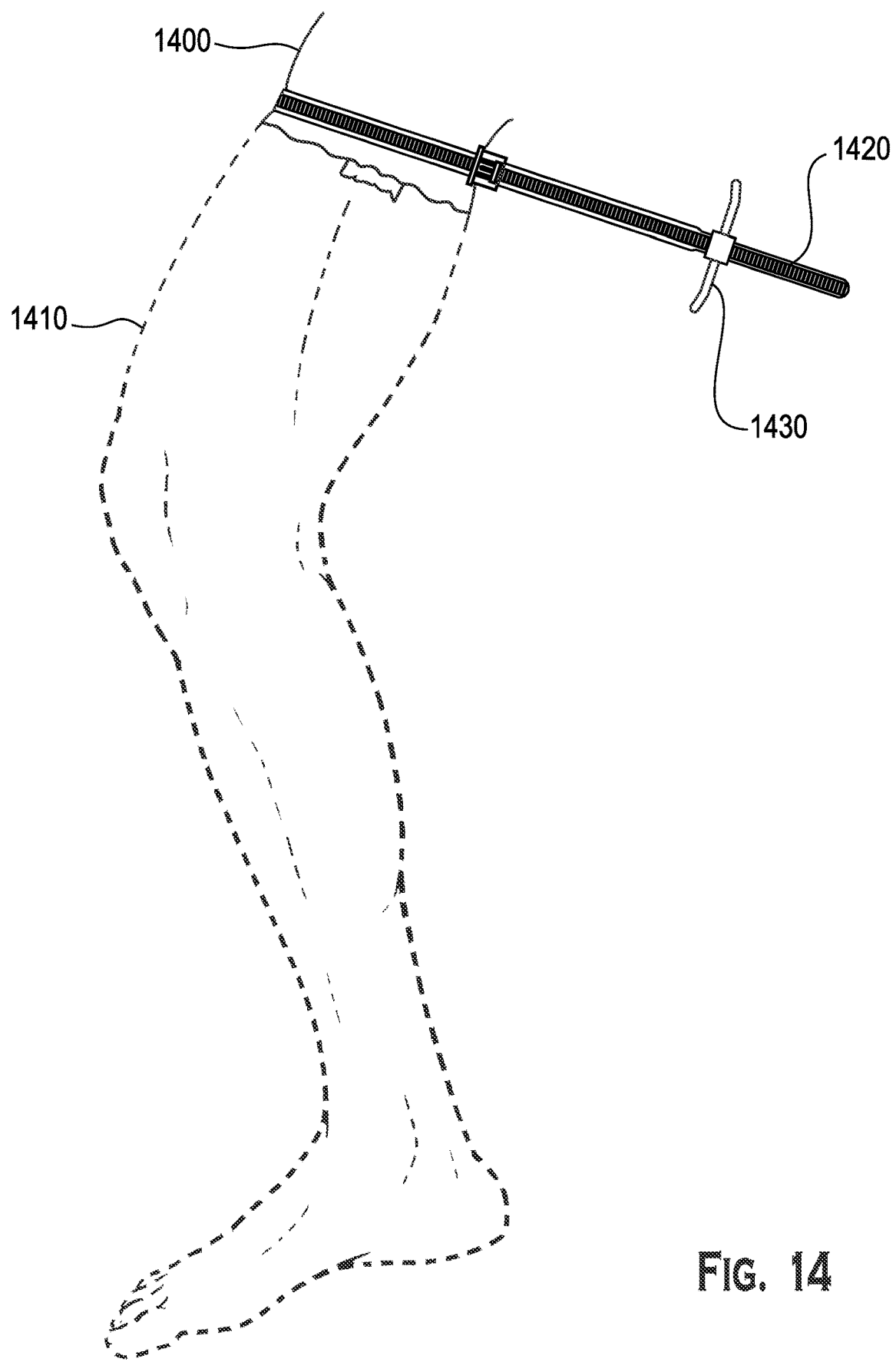
FIG. 14 illustrates a front view of an example releasable tie used as a tourniquet for an amputated leg, according to one embodiment.

FIG. 14 illustrates a front view of an example releasable tie 1420 being used as a tourniquet on an amputated leg 1400. The leg 1400 has been amputated around a top of the upper leg (thigh) so that the amputated portion 1410 (illustrated with a dotted line) includes the foot, the lower leg, the knee and a portion of the upper leg. The tie 1420 is secured to the leg 1400 below the amputation. A handle 1430 secured to the strap (not separately labeled) after the tie 1420 has been wrapped around the leg 1400 is used to provide a sufficient amount of leverage and grip to pull the tie 1420 tight enough.

FIGS. 15A-D illustrate several views of an example releasable tie 1500 and an example tightening handle 1550 that can be used to provide sufficient leverage to tie the tie tight enough to act as a tourniquet. The tie 1500 includes teeth 1510 on one end of the strap (not separately labeled). The teeth 1510 are surrounded by guiderails 1520, 1530. The guiderails 1530 toward an end of the strap are thinner than the guiderails 1520. The different sized guiderails 1520, 1530 prevent the handle 1550 from sliding too far down the strap. That is, the handle can go no further on the strap than the guiderails 1520. This is done to ensure that the handle 1550 does not get in the way of the releasable locking head 60 (not illustrated) or get too close to the body part being wrapped.

The handle 1550 includes a main body 1560 and arms 1590 extending therefrom. The main body 1560 includes a passthrough 1570 that the strap of the tie 1500 can passthrough (until it reaches the guiderail 1520). A latch 1575 having locking teeth 1580 is formed adjacent to the passthrough 1570 so that the teeth 1580 extend into the passthrough 1570 in order to engage the strap teeth 1510. The engagement of the latch teeth 1580 and the strap teeth 1510 allow the strap to pass through the handle 1550 in only one direction. As such, the handle 1550 can be placed on the strap but cannot be removed therefrom. This secures the handle 1550 to the tie 1500 and allows the handle 1550 to be used to tighten the tie 1500 as necessary. Once the handle 1550 is secured to the strap, a user can grab the arms 1590 and pull away to tighten the tie 1500.

The main body 1560 may also include an opening 1585 adjacent the latch 1575 to allow the latch 1575 to flex when the strap is passing through the passthrough 1570. According to one embodiment, the opening 1585 may enable a user to disengage the latch teeth 1580 and the strap teeth 1510.

Figure 15D:
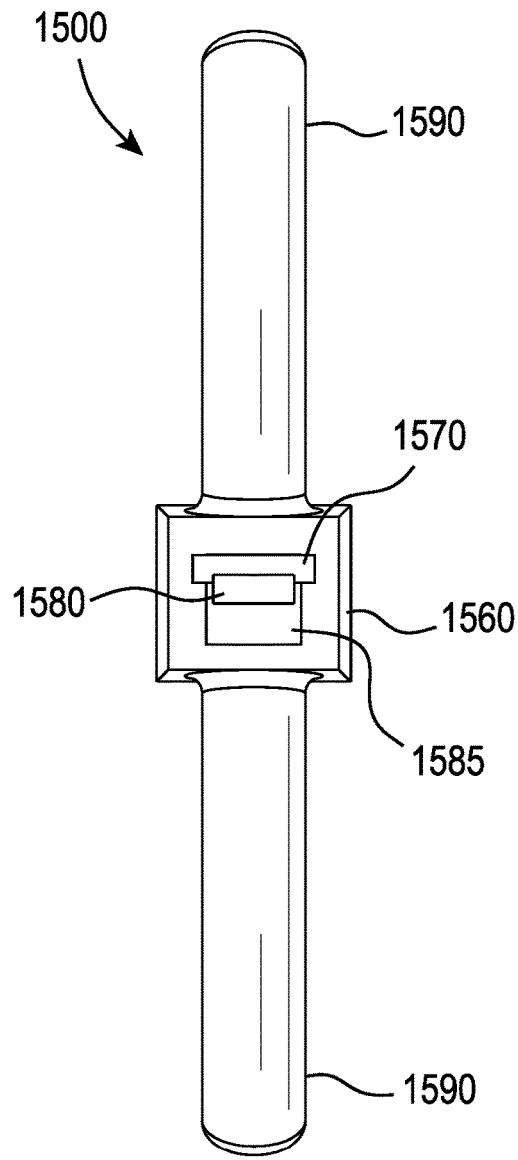

FIG. 15A illustrates a perspective view of the example handle 1550 being aligned with the example strap of the example tie 1500 for placement thereon. FIG. 15B illustrates a perspective view of the example handle 1550 located on the example strap. FIG. 15C illustrates a cross-sectional view of FIG. 15B. FIG. 15D illustrates a top view of the example handle 1550.

Figure 16A:
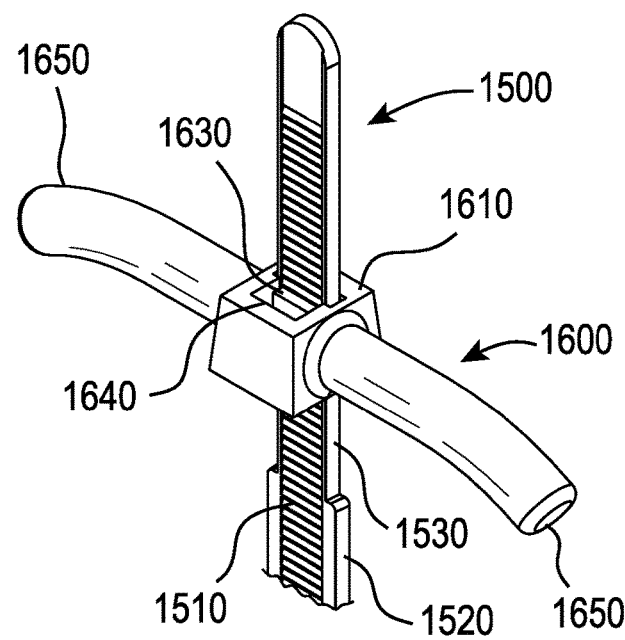
FIGS. 16A-B illustrate perspective and top views of an example releasable tie and an example tightening handle, according to one embodiment.
Figure 16B:
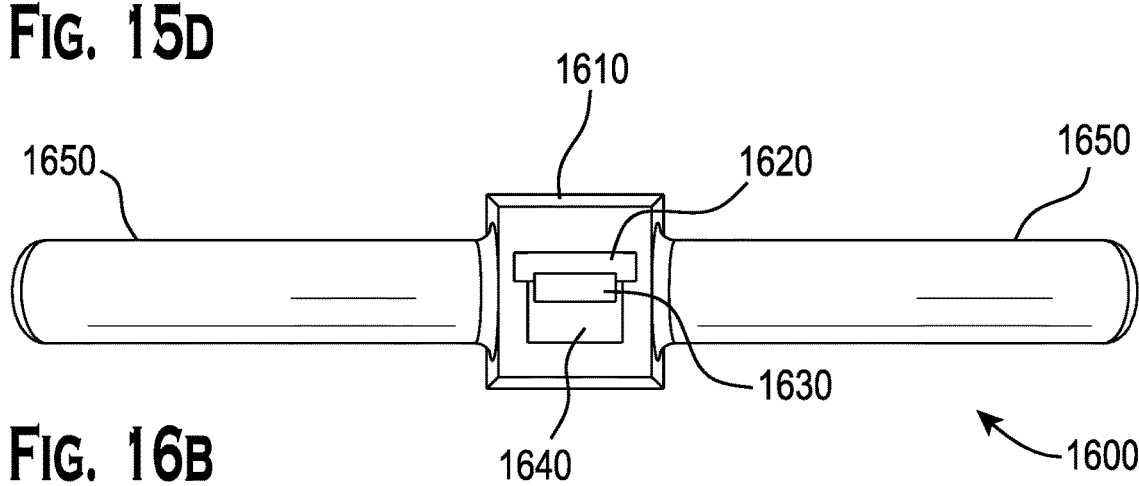

FIG. 16A illustrates a perspective view of an example tightening handle 1600 being placed on the example releasable tie 1500. FIG. 16B illustrates a top view of the example tightening handle 1600. The tightening handle 1600 is similar to the tightening handle 1550 but has the arms 1650 parallel to the strap instead of perpendicular. The handle 1600 includes a main body 1610, a passthrough 1620, a latch (not visible) having at least one latch tooth 1630 extending into the passthrough 1620, an opening 1640 adjacent to the latch, and a pair of arms 1650. The passthrough 1620 is parallel to the arms 1650 so that the strap passes through parallel to the arms 1650.

Figure 17A:
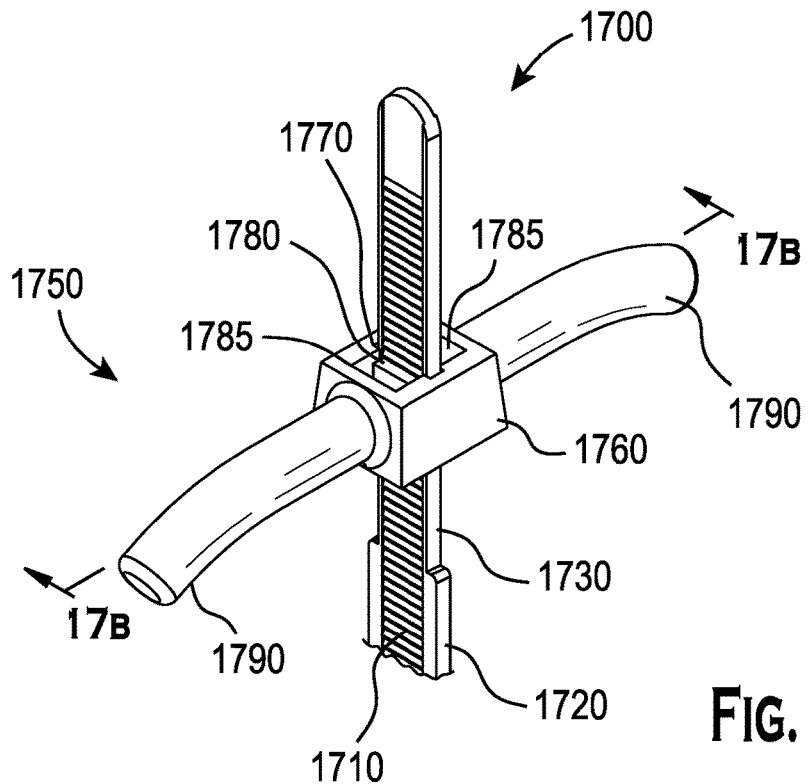
FIGS. 17A-B illustrate perspective and cross-sectional views of an example releasable tie and an example tightening handle, according to one embodiment.
Figure 17B:
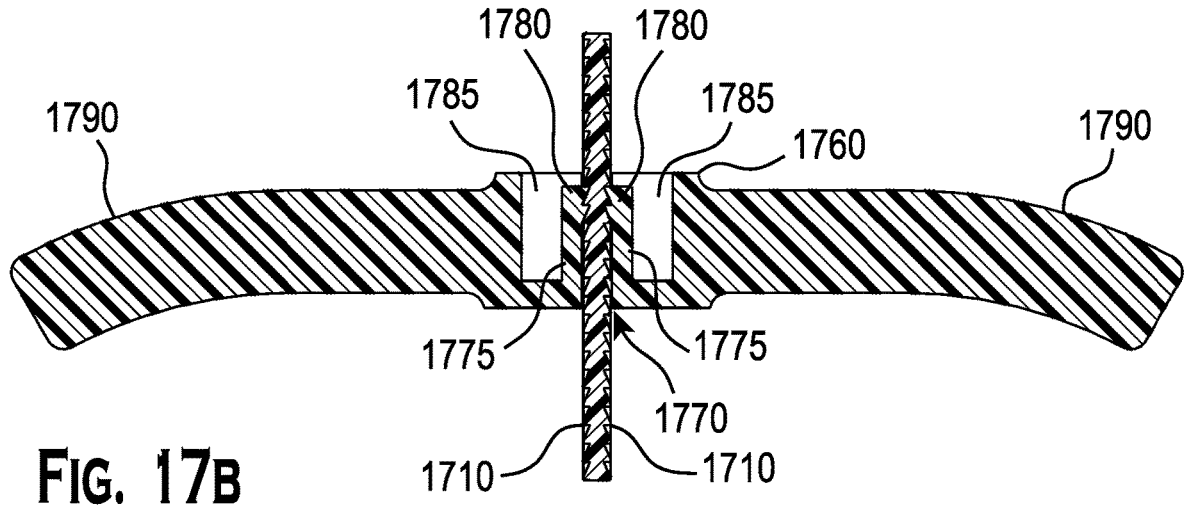

FIG. 17A illustrates a perspective view of an example handle 1750 located on an example tie 1700. FIG. 17B illustrates a cross-sectional view of FIG. 17A. The tie 1700 is similar to the tie 1500 except that it includes teeth 1710 on both sides thereof. The handle 1750 includes a main body 1760 and arms 1790 extending therefrom. The main body 1760 includes a passthrough 1770 that the strap of the tie 1700 can passthrough (until it reaches the guiderail 1720). Latches 1775 having locking teeth 1780 are formed adjacent to each side of the passthrough 1770 so that the teeth 1780 extend into the passthrough 1770 in order to engage each set of the strap teeth 1710. The main body 1760 may also include openings 1785 adjacent the latches 1775 to allow the latches 1575 to flex when the strap is passing through the passthrough 1770. According to one embodiment, the openings 1785 may enable a user to disengage the latch teeth 1780 and the strap teeth 1710.

FIG. 18A illustrates a perspective view of an example handle 1800 located on the example tie 1500. FIG. 18B illustrates a cross-sectional view of FIG. 18A. The handle 1800 includes a main body 1810 and arms 1860 extending therefrom. The main body 1810 includes two passthroughs 1820A, 1820B that the strap of the tie 1500 can passthrough. The first passthrough 1820A enables the strap to pass through until it reaches the guiderail 1520. The second passthrough 1820B enables the strap that has passed through the first passthrough 1820A to be looped back and passthrough the second passthrough 1820B in the opposite direction. A latch 1830 is located between the first and second passthroughs 1820A, 1820B. The latch 1830 includes locking teeth 1840 on an upper end thereof that extends into the first passthrough 1820A in order to engage the strap teeth 1510. The main body 1810 may also include an opening 1850 adjacent the latch 1830 to allow the latch 1830 to flex when the strap is passing through the first passthrough 1820A.

FIG. 19 illustrates a cross-sectional view of an example handle 1800 located on the example tie 1500. The handle 1900 is similar to the handle 1800 except a latch 1930 has teeth 1940 on a lower end that extend into a second passthrough 1920B. In this embodiment, the engagement of the teeth is on the portion of the strap that is feedback through the handle 1900. This embodiment may lessen the stress on the teeth 1510, 1940 as the loop back provides support for the engagement of the handle 1900 and tie 1500.

The handle includes a main body 1910 and arms 1960 extending therefrom. The main body 1910 includes two passthroughs 1920A, 1920B. The first passthrough 1920A enables the strap to pass through until it reaches the guiderail 1520 and the second passthrough 1920B enables the strap to be looped back in the opposite direction. The latch 1930 is located between the first and second passthroughs 1920A, 1920B. The main body 1910 may also include an opening 1950 adjacent the latch 1930 to allow the latch 1930 to flex when the strap is passing through the second passthrough 1920A.

Figure 20A:
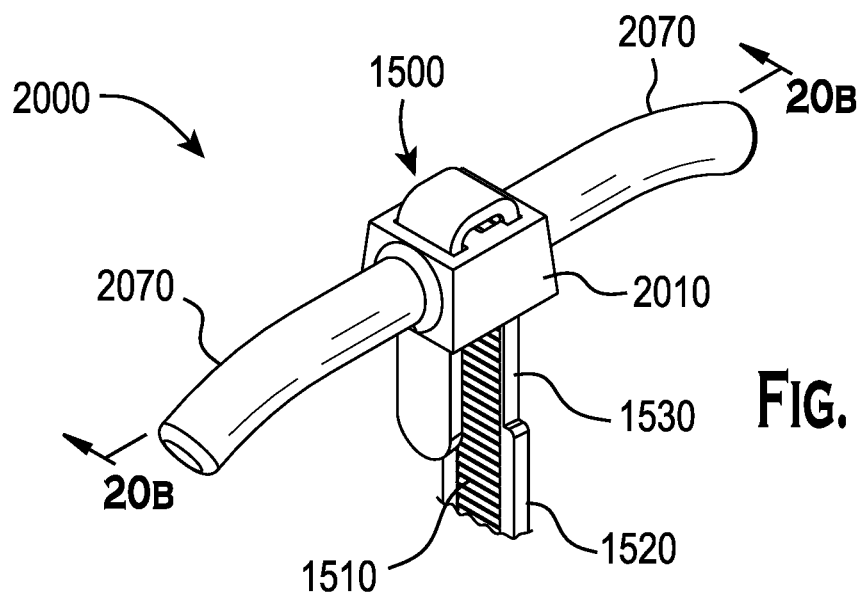
FIGS. 20A-B illustrate perspective and cross-sectional views of an example releasable tie and an example tightening handle, according to one embodiment.
Figure 20B:
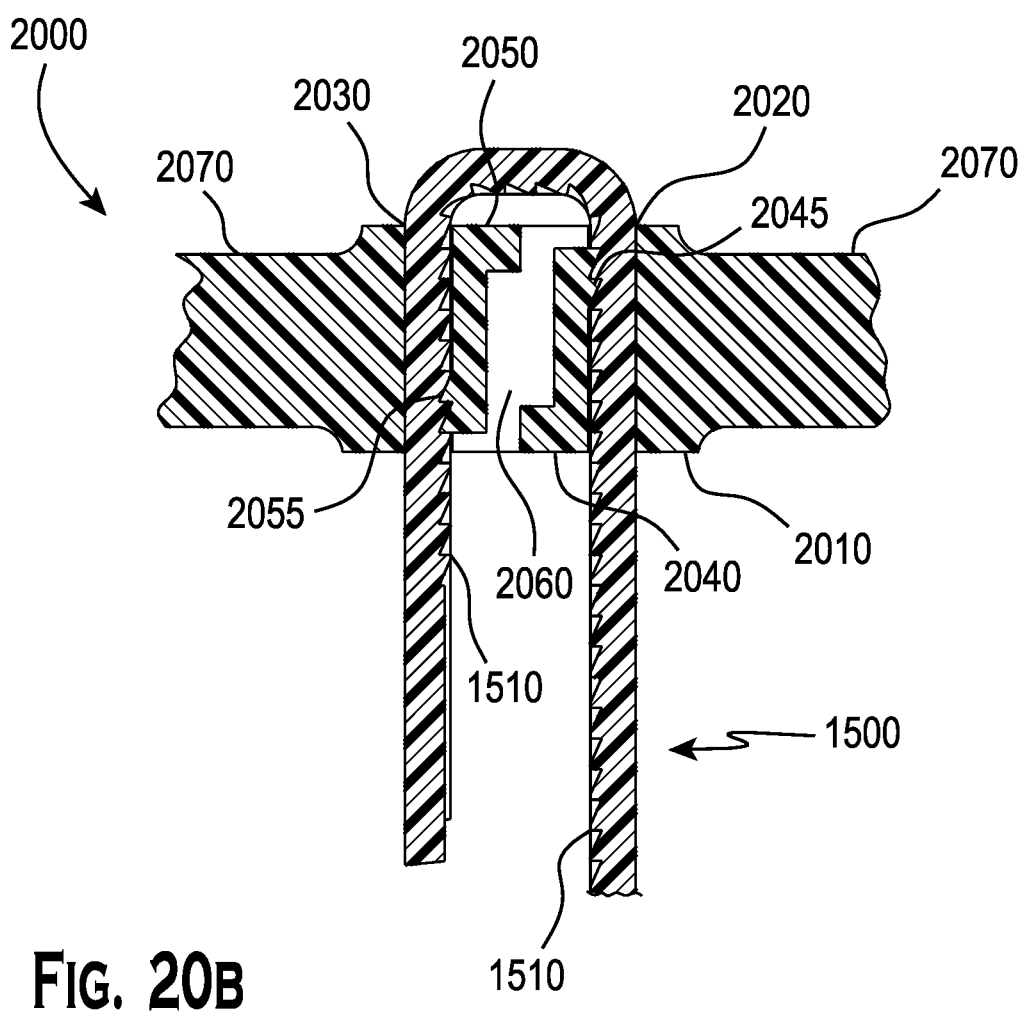

FIG. 20A illustrates a perspective view of an example handle 2000 located on the example tie 1500. FIG. 20B illustrates a cross-sectional view of FIG. 20A. The handle 2000 is a combination of the handle 1800 and the handle 1900 and includes two latches 2040, 2050 that each have teeth 2045, 2055 facing a respective passthrough 2020, 2030. This arrangement provides an engagement between the handle 2000 and the strap on the initial passthrough as well as the feedback.

The handle 2000 includes a main body 2010 and arms 2070 extending therefrom. The main body 2010 includes two passthroughs 2020, 2030 that the strap of the tie 1500 can passthrough. The first passthrough 2020 enables the strap to pass through until it reaches the guiderail 1520. The second passthrough 2030 enables the strap to be looped back and passthrough in the opposite direction. The latches 2040, 2050 are located between the first and second passthroughs 2020, 2030. The latch 2040 includes locking teeth 2045 on an upper end thereof that extend into the first passthrough 2020 in order to engage the strap teeth 1510. The latch 2050 includes locking teeth 2055 on a lower end thereof that extends into the second passthrough 2030 in order to engage the strap teeth 1510. The main body 2010 may also include an opening 2060 between the latches 2040, 2050 to allow the latches 2040, 2050 to flex when the strap is passing through the associated passthrough 2020, 2030.

Figure 21A:
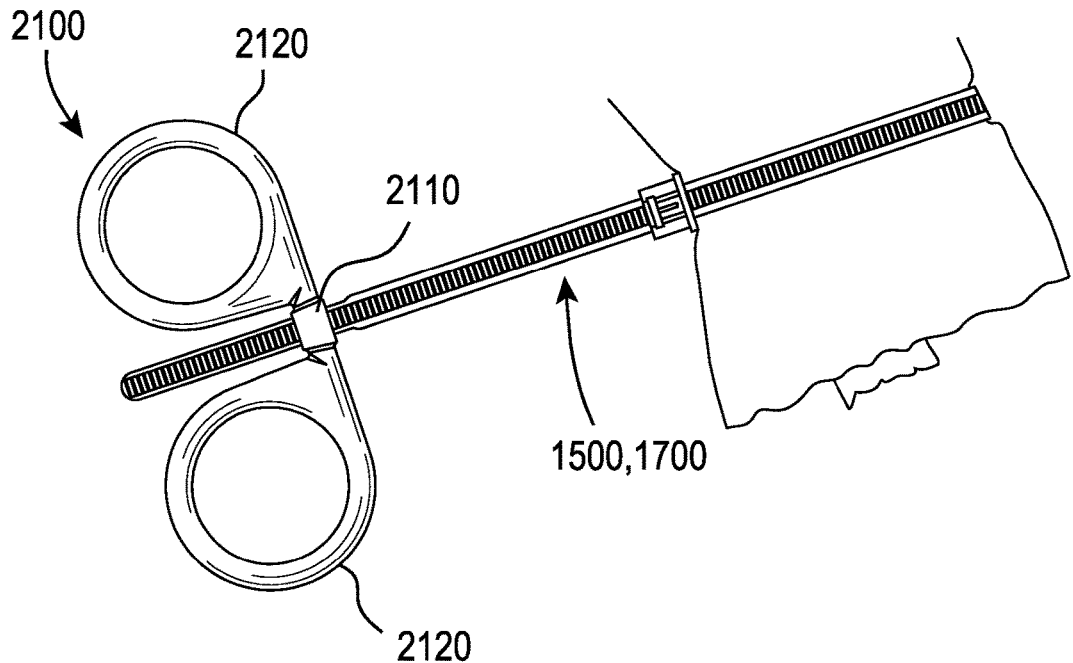
FIGS. 21A-B illustrate several views of an example releasable tie and an example tightening handle that can be used to provide sufficient leverage to tie the tie tight enough to act as a tourniquet, according to one embodiment.
Figure 21B:
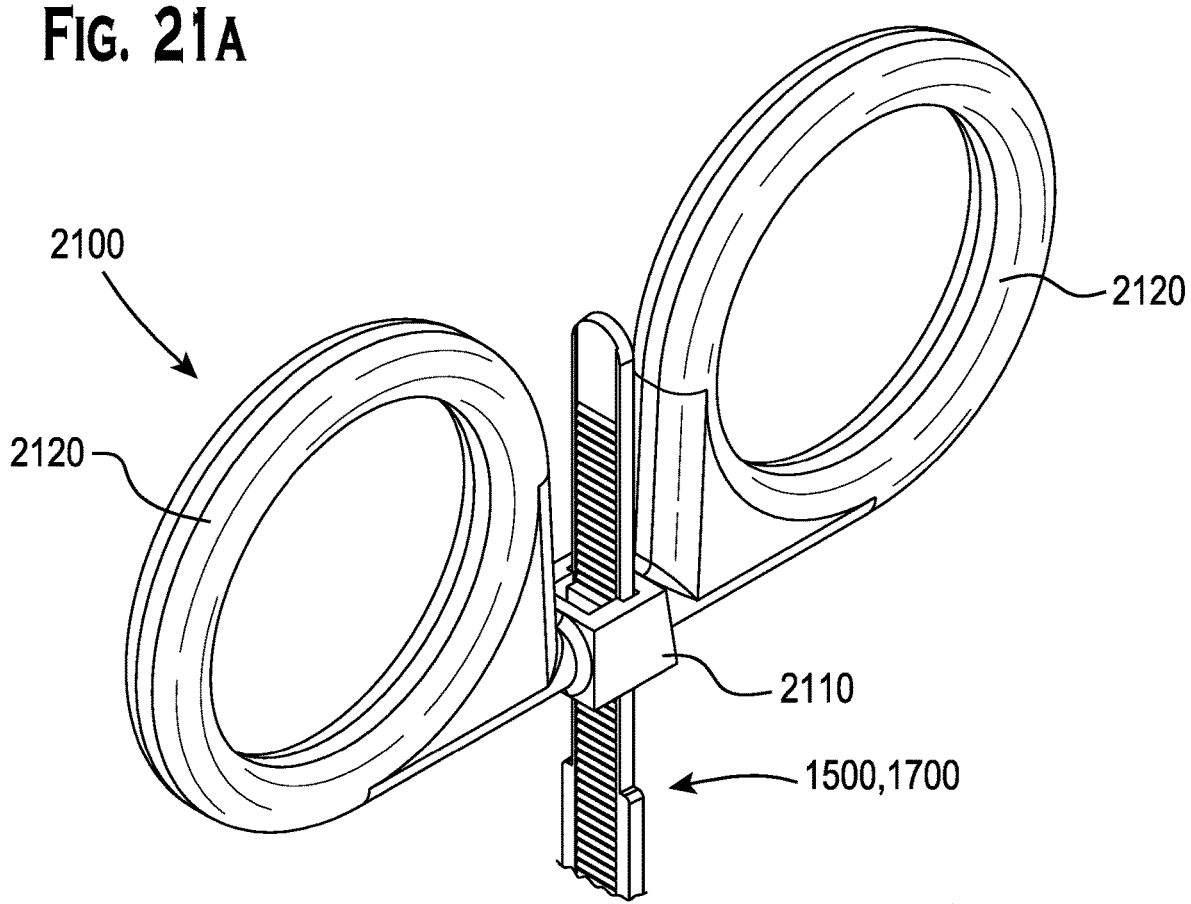

FIGS. 21A-B illustrate several views of an example releasable tie and an example tightening handle 2100 that can be used to provide sufficient leverage to tie the tie tight enough to act as a tourniquet. The tie can be any of the various embodiments of ties that have previously been previously disclosed in FIGS. 15A-20B including ties 1500, 1700. The manner in which the handle 2100 is connected to the tie can be any of the various embodiments previously disclosed in FIGS. 15A-20B. The handle 2100 includes a main body 2110 and a ring 2120 extending from each side thereof. The rings 2120 may be used in place of the arms that were illustrated in the various embodiments disclosed in FIGS. 15A-20B. The rings 2120 may provide more support for a user's fingers.

Figure 22C:
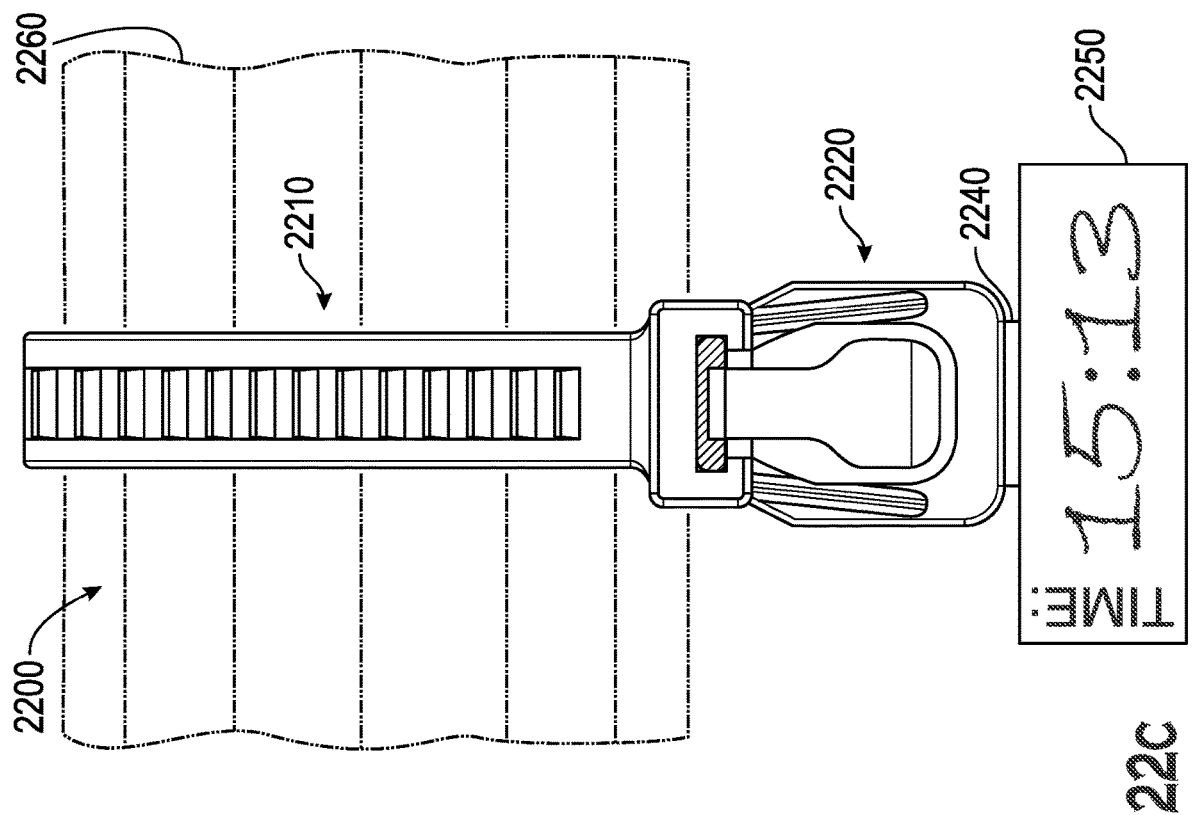
FIGS. 22A-C illustrate an example releasable tie that includes a label for recoding information related to, for example, when the tie was applied as a tourniquet, according to one embodiment.
Figure 22B:
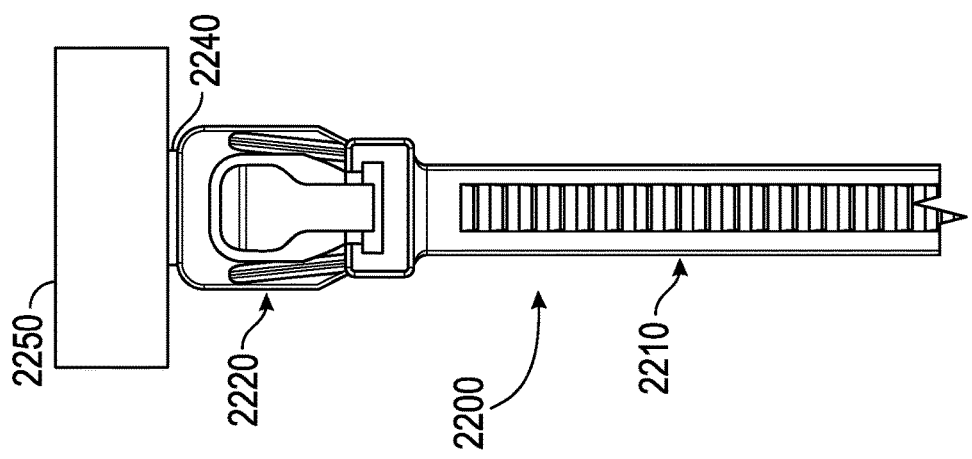
Figure 22A:
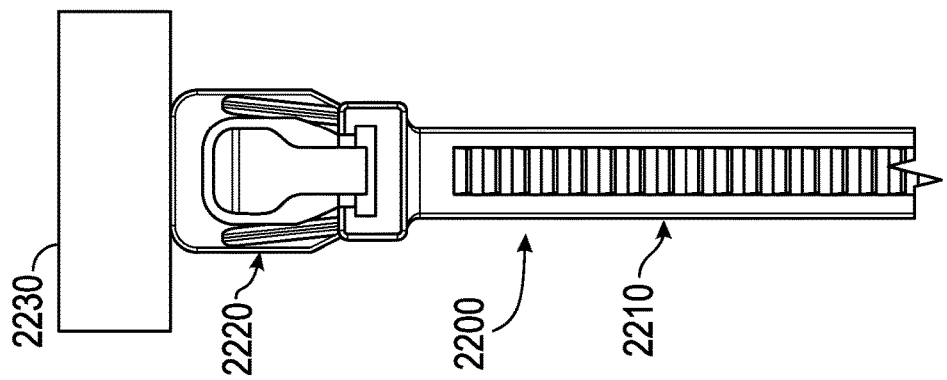

FIGS. 22A-C illustrate an example releasable tie 2200 that includes a label for recoding information related to, for example, when the tie was applied as a tourniquet. The tie 2200 includes a strap 2210 and a releasable locking head 2220. The specific components of the strap 2210 and the releasable locking head 2220 are not labeled for ease of illustration. FIG. 22A illustrates a label 2230 extending directly from a backplate of the locking head 2220. FIG. 22B illustrates a tab 2240 extending from the backplate of the locking head 2220 and a label 2250 extending from the tab 2240. FIG. 22C illustrates the tie 2200 wrapped around a body part 2260 and the time at which the tie 2200 was applied as a tourniquet recorded on the label 2250.

One or more ties and a handle may be provided as part of a tourniquet kit. The tourniquet kit may simply include the ties and the handle or may include other contents that may be used as part of a first aid kit.

Figure 23:
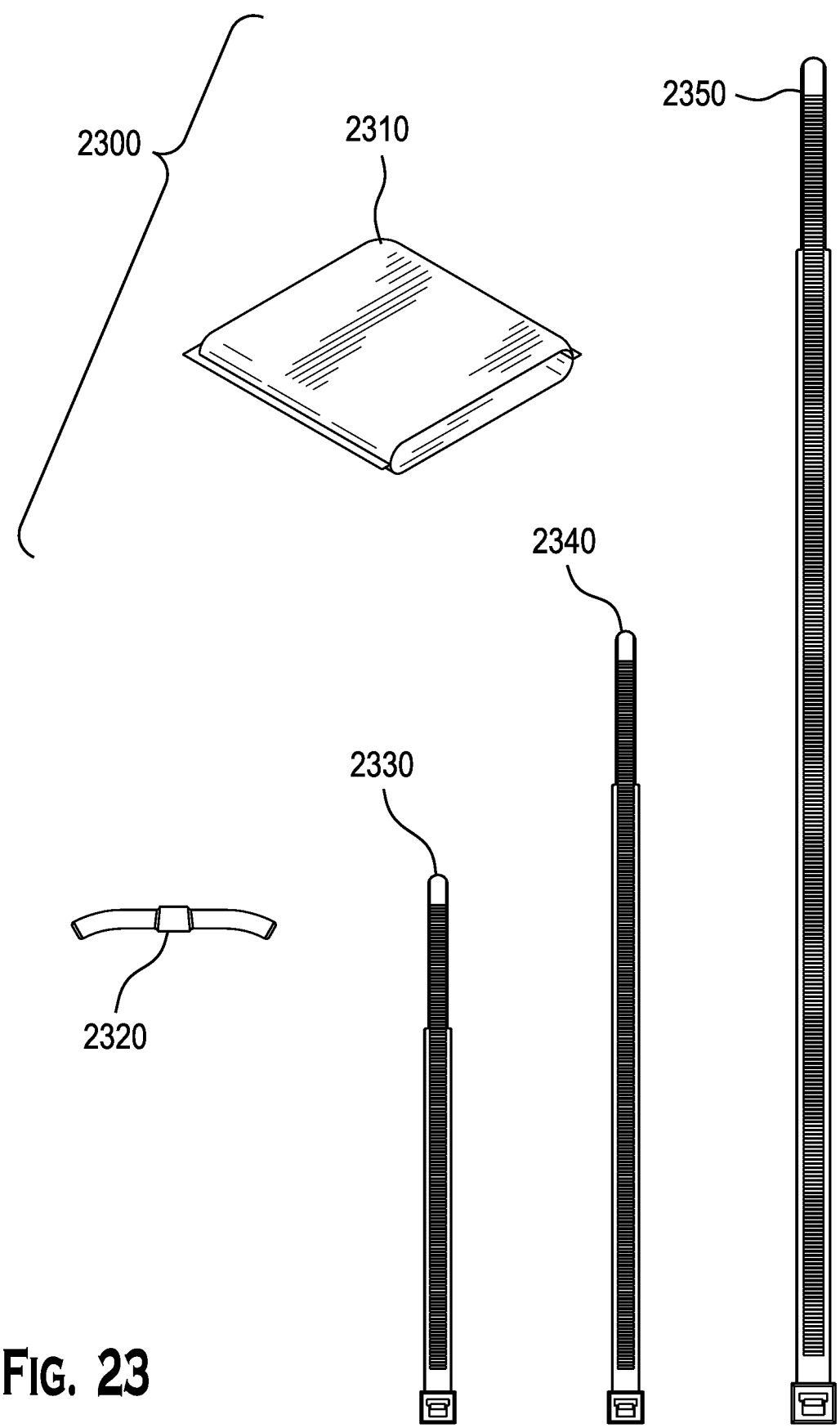
FIG. 23 includes an example kit, according to one embodiment.

FIG. 23 includes an example kit 2300. The kit 2300 may be provided within a sealed package 2310. The package 2310 may be a sterile package that is easy to open. Within the package 2310 may be a handle 2320 and one or more ties 2330-2350. As illustrated, there are three different sized ties that may be used for different body parts. For example, a first size may be used for fingers or like sized body parts, a second size may be used for arms or like sized body parts, and the third size may be used for legs or like sized body parts. It should be noted that the kit 2300 is not limited to any number or size of ties. Rather, any number and size of ties along with a handle can be provided without departing the current scope. Furthermore, the handle is illustrated as the handle with two arms but is not limited thereto. Moreover, the connection between the ties and the handle can be any configuration discussed herein or other configurations providing the same function. The ties 2330-2350 were not illustrated with labels but could include labels without departing the current scope. It is anticipated that the simple tie and handle kit 2300 may be utilized by medical personnel who would have other materials that may be required to provide aid to an individual already at their disposal and thus not be required within the kit.

Figure 24:
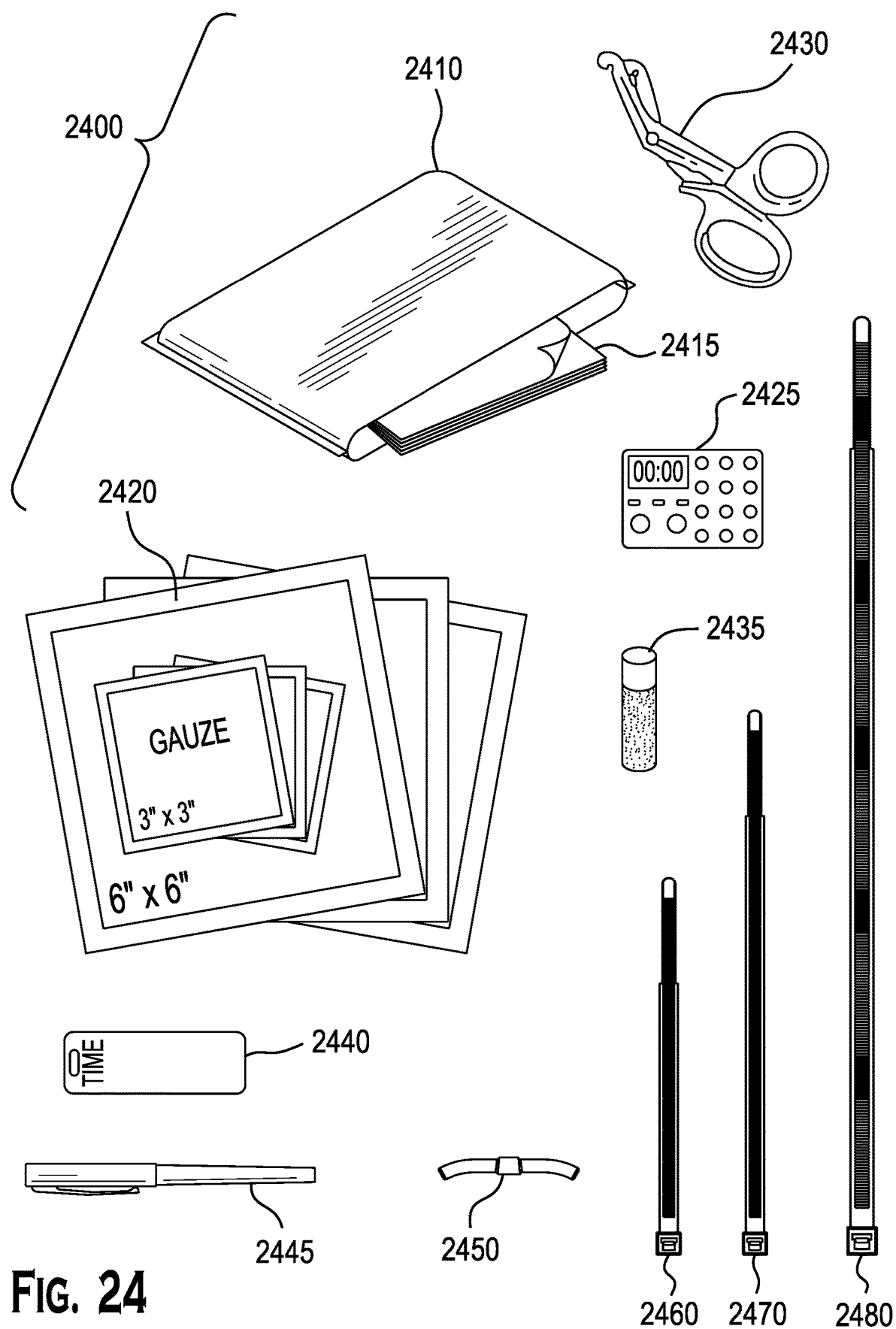
FIG. 24 includes an example kit that may be part of a first aid kit, according to one embodiment.

FIG. 24 includes an example kit 2400 that may be part of a first aid kit. The kit 2400 may be provided within a sealed package 2410. The package 2410 may be a sterile package that is easy to open. Within the package 2410 may be directions 2415, gauze 2420, a timer 2425, trauma scissors 2430, a clotting agent 2435, an attachable tag 2440 for recording, for example, time, a handle 2450 and one or more ties 2460-2480. The kit 2400 does not require all of these items and may include additional items without departing the current scope. As illustrated, there are three different sized ties but the kit 2400 is not limited to any number or size of ties. Furthermore, the handle is illustrated as the handle with two arms but is not limited thereto. Moreover, the connection between the ties and the handle can be any configuration discussed herein or other configurations providing the same function.

Although the invention has been illustrated by reference to specific embodiments, it will be apparent that the invention is not limited thereto as various changes and modifications may be made thereto without departing from the scope. Reference to "one embodiment" or "an embodiment" means that a particular feature, structure or characteristic described therein is included in at least one embodiment. Thus, the appearances of the phrase "in one embodiment" or "in an embodiment" appearing in various places throughout the specification are not necessarily all referring to the same embodiment.

The various embodiments are intended to be protected broadly within the spirit and scope of the appended claims.

The invention claimed is:

1. An adjustable tourniquet, comprising:
    an elongated planar strap having a plurality of strap teeth formed on at least one side thereof;
    a releasable locking head formed adjacent to a first end of the strap, wherein the locking head includes:
        a main body having a passthrough to receive a second end of the strap in a locking direction to form a loop to secure around a body part, wherein amount of the strap that traverses the opening controls size of the loop;
        at least one locking head tooth extending into the passthrough and being complementary to the plurality of strap teeth when the second end of the strap enters the passthrough, wherein the at last one locking head tooth is adapted to engage with at least one strap tooth for preventing movement of the strap in a release direction;
        a release tab engaged with a first side of the main body and having a first side connected to the at least one locking head tooth and a second side extending away from the first side of the strap, wherein the second side of the release tab is wider than the first side; and
        a backplate engaged with a first side of the main body and having a first side adjacent the passthrough and a second side extending away from the first side of the strap, wherein the backplate is substantially parallel to the release tab, wherein the backplate is wider and longer than the release tab, and wherein the backplate includes an opening therethrough larger than the release tab;
    wherein the release tab and backplate extend away from the loop secured around the body part when the strap is in the passthrough and are accessible by a user, wherein the release tab is configured to be depressed by a first finger of the user, wherein the backplate is configured to receive a second finger of the user to provide resistance when the release tab is depressed toward the backplate by the first finger, wherein the depressing of the release tab is to release the at least one locking head tooth from engagement with the at least one strap tooth to permit the strap to be moved in the release direction; and a handle connectable to the strap after the strap has been secured around the body part, wherein the strap is to provide more leverage to sufficiently tighten the adjustable tourniquet.

2. The apparatus of claim 1, wherein the locking head further includes a label extending therefrom to record information thereon.

3. The apparatus of claim 1, wherein the strap includes first guiderails and second guiderails, wherein the second guiderails are located at a second end of the strap and are smaller than the first guiderails, wherein the second guiderails enable the handle to receive the second end of the strap, and wherein the first guiderails stop the handle from proceeding any further on the strap.

4. The apparatus of claim 3, wherein length of the second guiderails determines how far the handle can be slid onto the strap.

5. The apparatus of claim 1, wherein the handle includes a main body having a passthrough formed therein and a latch having at least one tooth extending into the passthrough, wherein the latch and the at least one latch tooth enable the strap to move through the passthrough in a first direction that enables the handle to be located on the strap but prevents the strap from moving a second direction to remove the handle.

6. The apparatus of claim 5, wherein the strap includes teeth on each side of the second end and the handle includes two latches where each latch has at least one tooth extending into opposite sides of the passthrough so that the handle is secured to the strap via the engagement of two sets of strap teeth and latch teeth.

7. The apparatus of claim 1, wherein the handle includes a main body having a first and a second passthrough formed therein, wherein the first passthrough enable the handle to be placed on the strap and the second passthrough enables the excess strap to be looped back through the handle.

8. The apparatus of claim 7, wherein the handle further includes a latch having at least one tooth extending into the first passthrough, wherein the latch and the at least one latch tooth enable the strap to move through the first passthrough in a first direction that enables the handle to be located on the strap but prevents the strap from moving a second direction thus securing the handle to the strap.

9. The apparatus of claim 7, wherein the handle further includes a latch having at least one tooth extending into the second passthrough, wherein the latch and the at least one latch tooth enable the strap to move through the second passthrough in a first direction but prevents the strap from moving a second direction thus securing the handle to the strap.

10. The apparatus of claim 7, wherein the handle further includes a first latch having at least one tooth extending into the first passthrough and a second latch having at least one tooth extending into the second passthrough.

11. The apparatus of claim 1, wherein the handle includes a main body to receive the strap and arms extending therefrom.

12. The apparatus of claim 1, wherein the handle includes a main body to receive the strap and loops extending therefrom.

13. A medical kit including a sealed package containing at least one of the apparatus of claim 1.

14. The medical kit of claim 13, further including at least some subset of directions, gauze, a timer, trauma scissors, a clotting agent, and an attachable tag.

15. A method of providing a releasable tourniquet around a body part, the method comprising:

providing an elongate planar strap having a plurality of strap teeth formed on at least one side and a locking head formed on one end; and securing the strap around the body part by
inserting an opposite end of the strap into an opening in the locking head in a locking direction and forming a loop to receive the body part, wherein amount of the strap that traverses the opening controls size of the loop;

locking the strap in the locking head by engaging at least one lock tooth formed extending into the opening in the locking head with a complementary at least one of the strap teeth to prevent movement of the strap in a release direction;

placing a handle on the second end of the strap; and pulling the strap with the handle to adequately tighten the strap around the body part so as to act as a tourniquet.

16. The method of claim 15, further comprising loosening the strap from body part by depressing with a first finger a release tab pivotally connected to the at least one lock tooth while placing a second finger on a backplate that is positioned below the release tab to provide resistance while the release tab is being depressed to disengage the least one lock tooth from the at least one strap tooth; and securing the releasable latch between the first and the second finger and pulling the releasable latch in a direction away from the loop.

17. The method of claim 15, wherein the placing a handle on the second end of the strap includes passing the strap through a passthrough in the handle, wherein the handle includes a latch having teeth aligned to engage with the strap teeth.

18. The method of claim 15, wherein the placing a handle on the second end of the strap includes passing the strap through a first passthrough in the handle and then looping the strap back through a second passthrough in the handle, wherein the handle includes a latch having teeth aligned to engage with the strap teeth in at least one of the first and the second passthrough.

19. The method of claim 15, wherein the strap has teeth of both ends of a second end thereof, and wherein placing a handle on the second end of the strap includes passing the strap through a passthrough in the handle, wherein the handle includes a first and a second latch located on opposite sides of the passthrough, wherein each of the first and the second latches has teeth aligned to engage with the strap teeth on each side of the strap.

20. The method of claim 15, wherein the strap includes first guiderails and second guiderails, wherein the second guiderails are located at a second end of the strap and are smaller than the first guiderails, and wherein placing a handle on the second end of the strap includes placing the handle onto the strap over the second guiderails until the first guiderails prevent the handle from proceeding any further on the strap.

* * * * *